United States Patent [19]

Rokach et al.

[11] 4,394,515

[45] Jul. 19, 1983

[54] 10,11-DIHYDRO-11-OXODIBENZO[b,f]-THIEPIN COMPOUNDS

[75] Inventors: Joshua Rokach, Chomedey-Laval, Canada; Clarence S. Rooney, Worcester; Edward J. Cragoe, Jr., Lansdale, both of Pa.

[73] Assignee: Merck & Co., Inc., Rahway, N.J.

[21] Appl. No.: 251,221

[22] Filed: Apr. 6, 1981

Related U.S. Application Data

[63] Continuation of Ser. No. 917,211, Jun. 23, 1978, abandoned, which is a continuation-in-part of Ser. No. 819,200, Jul. 26, 1977, abandoned.

[51] Int. Cl.$^3$ ............................................ C07D 337/14
[52] U.S. Cl. .................................... 549/12; 548/252; 548/253; 424/269; 424/275
[58] Field of Search ........................................... 549/12

[56] References Cited

U.S. PATENT DOCUMENTS

| | | | |
|---|---|---|---|
| 3,509,154 | 4/1970 | Fouche | 544/378 |
| 3,905,989 | 9/1975 | Hodson | 548/253 |
| 4,025,635 | 5/1977 | Hodson | 424/269 |

*Primary Examiner*—Donald G. Daus
*Assistant Examiner*—D. B. Springer
*Attorney, Agent, or Firm*—Ernest V. Linek; Hesna J. Pfeiffer; Thomas E. Arther

[57] ABSTRACT

Novel 7- and 8-R-10,11-dihydro-11-oxodibenzo[b,f]-thiepin derivatives are employed in the treatment and control of allergic conditions such as allergic asthma.

2 Claims, No Drawings

10,11-DIHYDRO-11-OXODIBENZO[B,F]THIEPIN COMPOUNDS

This is a continuation of application Ser. No. 917,211, filed June 23, 1978, now abandoned, which in turn is a continuation-in-part of application Ser. No. 819,200, filed July 26, 1977, now abandoned.

SUMMARY OF THE INVENTION

This invention relates to prostaglandin antagonists useful in treating a variety of conditions, such as allergic asthma where excessive contractile activity of prostaglandins and prostaglandin biosynthetic intermediates occur. These prostaglandin antagonists are 7- and 8-substituted-10,11-dihydro-11-oxodibenzo[b,f]thiepins having the structural formula:

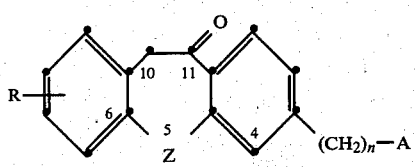

wherein n is an integer from 0 to 4: Z is thio, sulfinyl, or sulfonyl; R is hydrogen, halogen including chloro, bromo, fluoro and iodo, amino, $C_1$ to $C_4$ alkyl, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, trifluoromethylthio, cyano, carboxy, nitro and $C_1$ to $C_4$ alkyl or dialkylamino; A is 5-tetrazolyl, 3-hydroxy-1,2,5-thiadiazol-4-yl, 4-hydroxy-$\Delta^3$-pyrroline-3-yl-2,5-dione or

wherein $R_2$ is hydroxy, loweralkoxy, N,N-diloweralkylaminoloweralkoxy, hydroxyloweralkoxy, carboxyloweralkoxy, amino, N-loweralkylamino, N,N-diloweralkylamino, loweralkylsulfonylamino, carboxyloweralkylamino, carboxamidoloweralkylamino and 2-imino-3-methylthiazolidine with the proviso that $R_2$ is not hydroxy when n is O and R is hydrogen; and the pharmaceutically acceptable salts thereof.
chlorine, bromine, iodine and fluorine. Unless otherwise specifically stated, the terms, loweralkyl and loweralkoxy, include straight and branched chain alkyl and alkoxy groups having 1 to 4 carbon atoms in the alkyl or alkoxy moiety such as, for example, methyl, ethyl, n-propyl, isopropyl, n-butyl, methoxy, ethoxy, n-propoxy and isobutoxy. The term, loweralkanoyl, includes straight or branched chain alkanoyl groups having 1 to 4 carbon atoms in the alkanoyl moiety such as, for example, formyl, acetyl, propanoyl, isobutyryl and isobutyryl.

These dibenzo[b,f]thiepin derivatives antagonize the actions of contractile prostaglandins, such as $PGF_2$, $PGG_2$ and $PGH_2$ and $TXA_2$. The use of agents which act as prostaglandin antagonists offers new approaches to therapy in a number of disease states. For example, certain prostaglandins, such as $PGF_{2\alpha}$, $PGG_2$ and $PGH_2$, are potent contractants of bronchial muscle. Indeed human asthmatics have been shown to be especially sensitive to the bronchial constricting action of $PGF_{2\alpha}$.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, premature abortion, and dismenorrhea.

In addition to the prostaglandin antagonist actions, the dibenzo[b,f]thiepins of this invention are antagonists of slow reacting substance of anaphylaxis (SRS-A). This contractile substance is released in the lung tissue in allergic asthma, and antagonism of its actions contributes to alleviation of this disease.

The dibenzo[b,f]thiepins of this invention are prepared according to the following general reaction scheme.

An appropriately substituted mercaptobenzoic acid II is reacted with m-dibromobenzene III ($R_3$=Br) to obtain the 0-(3-bromophenyl)benzoic acid IV. Or alternatively, an appropriately substituted o-bromobenzoic acid II ($R_2$=Br) is reacted with m-bromobenzethiol III ($R_3$=SH) to give IV,

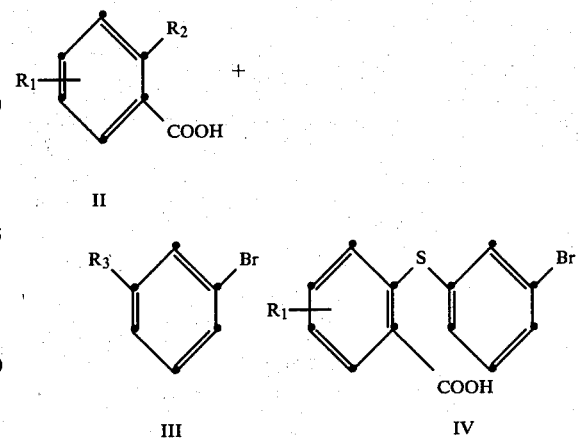

where $R_1$ is hydrogen, nitro, amino, $C_1$ to $C_4$ alkanoyl, hydroxyl, $C_1$ to $C_4$ alkoxy, $C_1$ to $C_4$ alkylsulfinyl, $C_1$ to $C_4$ alkylsulfonyl and $C_1$ to $C_4$ alkyl, trifluoromethyl and trifluoromethylthio. $R_2$ and $R_3$ are different and alternatively are thiol and bromo.

Generally, the sulfide-forming reaction is carried out according to the methods described by Jilek et al., Monatsh. Chem. 96, 200 (1965), Protiva et al, Czech. Pat. No. 121,337 C.A. 68 (105, 247t, 1968) and U.S. Pat. No. 3,711,489, and by other procedures well known in the art.

The resulting o-(3-bromophenylthio)benzoic acid (IV) is reduced to the alcohol, brominated, and the bromo replaced with cyano. The cyano derivative is then hydrolyzed to the carboxylic acid V.

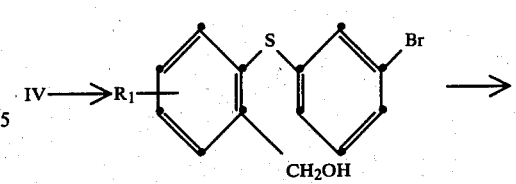

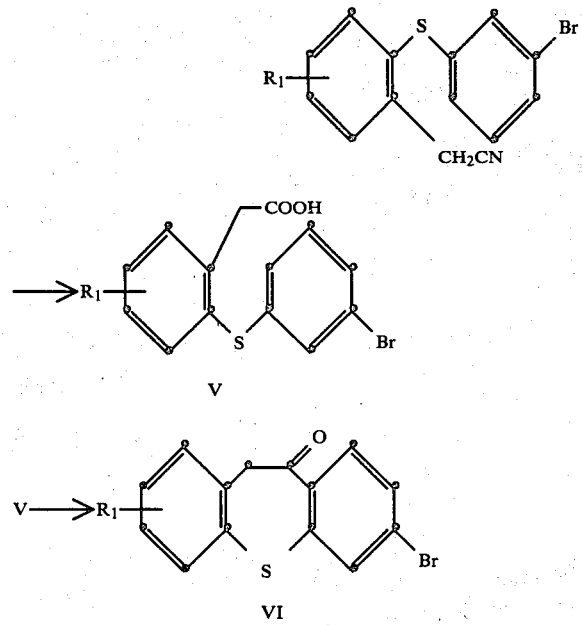

V

VI

The carboxylic acid V is transformed into the 3-bromo-11-oxo-10,11-dihydrodibenzo[b,f]thiepin by first conversion to the acid halide with thionyl or phosphoryl halide followed by Friedel-Crafts cyclization with a Lewis acid such as aluminum chloride to give VI. Reduction of the ketone VI with alkali metal borohydrides, followed by heating with catalytic amounts of a mineral acid, such as sulfuric acid or toluenesulfonic acid provides the 3-bromodibenzo[b,f]thiepin VII.

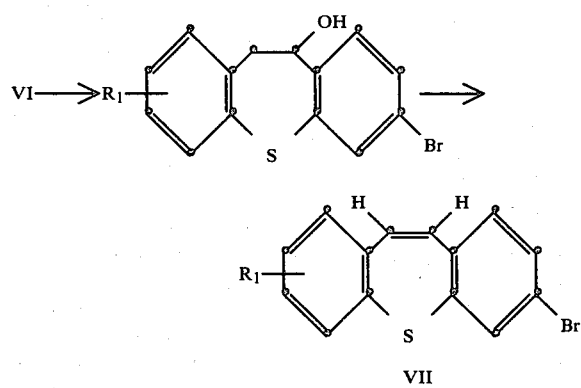

VII

The 3-bromo derivative VII is then converted to the 3-nitrile VIII by reaction with cuprous cyanide in a high boiling polar solvent such as dimethylformamide, N-methylpyrrolidone and the like.

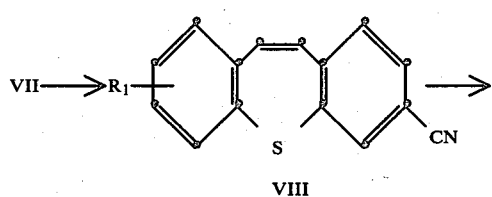

VIII

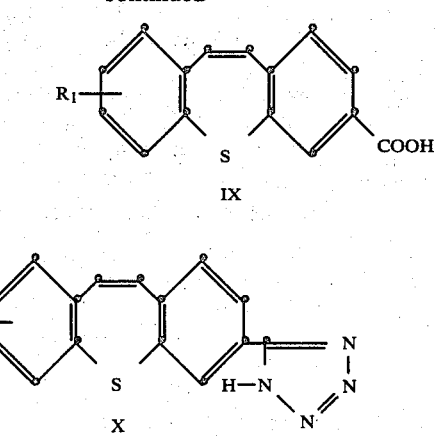

IX

X

The 3-cyano derivative VIII may be hydrolyzed with aqueous mineral acid or base to give the dibenzo[b,f]-thiepin-3-carboxylic acid IX. The 3-cyano compound VIII may also be reacted with azide ion at reflux in an inert solvent such as dimethylformamide, hexamethylphosphorictriamide and the like for ¼ to 18 hours to give the tetrazole derivative X. Alternatively, the cyano intermediate VIII may be oxidized with organic peroxides such as peroxy acids, for example, m-chloroperbenzoic acid and the like, in a stepwise fashion to the corresponding sulfoxide XI and sulfone XII, controlling the molar ratio of oxidant to reductant. This determines the oxidation level of the sulfur. For exxample, a 1:1 molar ratio results largely in the production of sulfoxide XI. In contrast, a 2 to 3 molar excess of oxidant results in a yield predominantly comprising the sulfone XII.

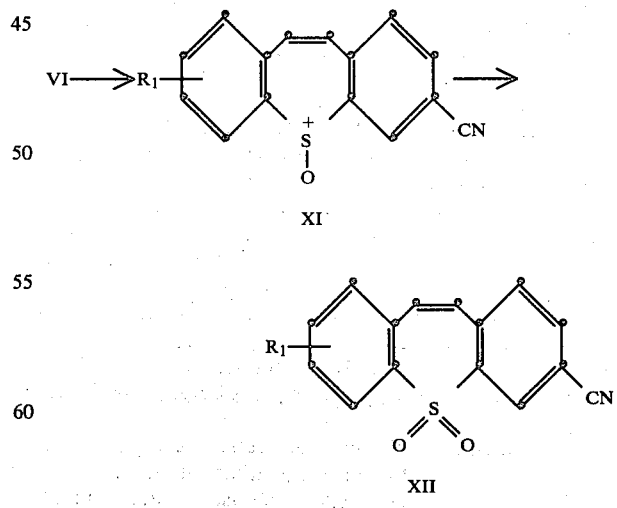

XI

XII

Hydrolysis of XI and XII using aqueous mineral acid or alkali provides the corresponding carboxylic acids XIII and XIV.

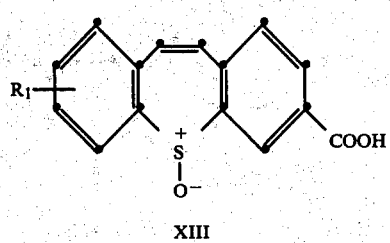

XIII

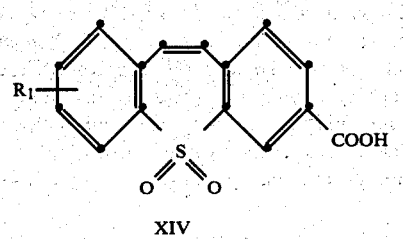

XIV

Reaction of XI and XII with azide ion as described above provides the tetrazoles XV and XVI, respectively,

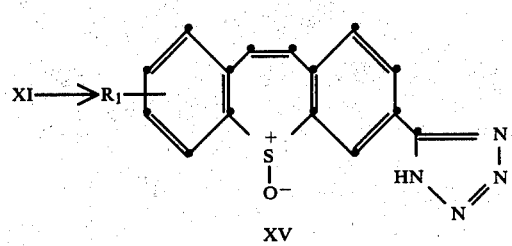

XV

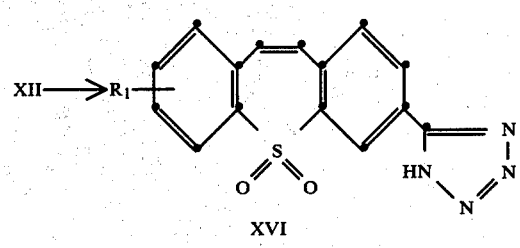

XVI

Compunds of type I where the 10-11 double bond is saturated are prepared from intermediate V in which the 3-bromo is converted to a cyano derivative XVII, then hydrolyzed with mineral acid to the acid XVIII and esterified to the ester XIX, where R' is loweralkyl.

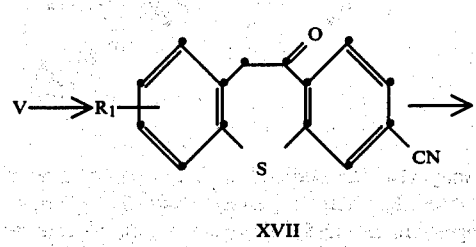

XVII

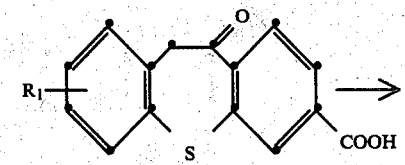

XVIII

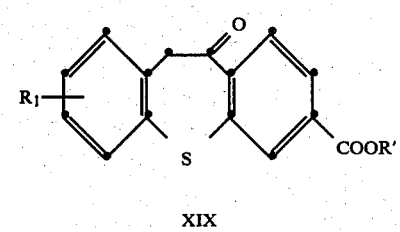

XIX

The ester XIX is reduced by conventional methods, e.g., Wolff-Kishner, to compound XXII or better by reduction with NaBH₄ to XX followed by PBr₃ reaction to XXI, then reduction with NaBH₄ in solvent such as sulfolane to XXII.

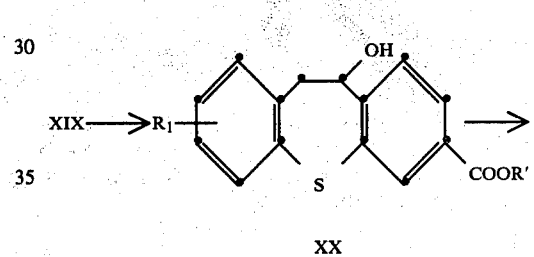

XX

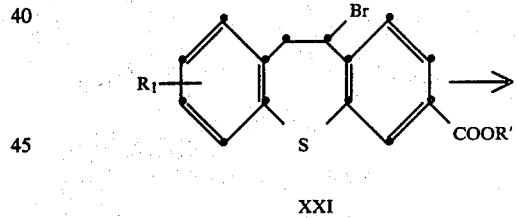

XXI

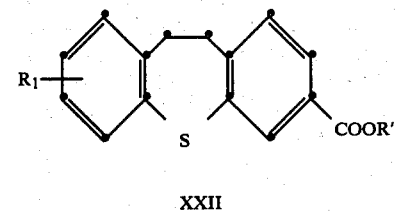

XXII

Compound XXII may be hydrolyzed with aqueous mineral acid or base to give the 10,11-dihydro[b,f]thiepin-3-carboxylic acid XXIII. Compound XXII may also be oxidized with one equivalent of organic peroxides, such as peroxy acids, for example, m-chloroperbenzoic acid and the like, to yield the sulfoxide XXIV, which can then be hydrolyzed with mineral acid or base to provide the carboxylic acid XXV.

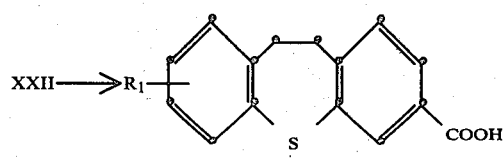

XXIII

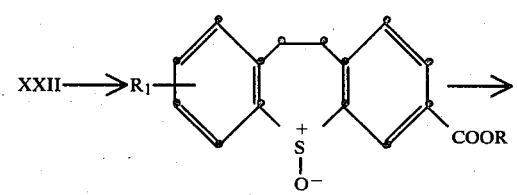

XXIV

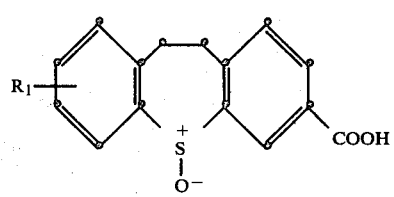

XXV

The acid XXIII may be oxidized with excess organic peroxides such as hydrogen peroxide in acidic solvents such as acetic acid at temperatures ranging from 0°–100° C. to yield compound XXVI.

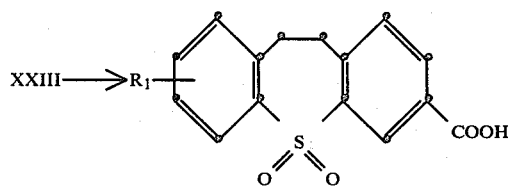

XXVI

Compound VI may be reacted with phosphorous tribromide followed by reduction with NaBH₄ in solvents, such as sulfolane, and reaction with cuprous cyanide in high boiling polar solvents, such as dimethylformamide, N-methylpyrrolidone and the like, to yield XXVII.

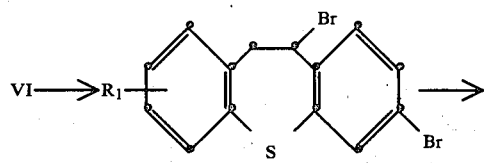

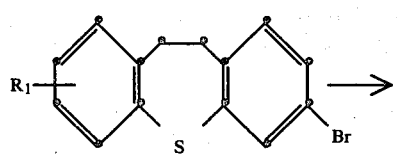

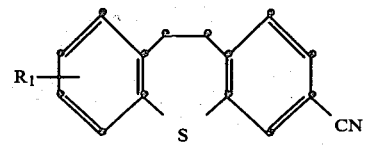

XXVII

The 3-cyano derivative XXVII may be reacted with azide ion at reflux in an inert solvent such as dimethylformamide or in THF with the addition of Lewis acid, such as AlCl₃, to yield the tetrazole derivative XXVIII. Compound XXVII can also be oxidized with excess peroxy acid, such as m-chloroperbenzoic acid followed by the tetrazole forming reaction to yield XXIX.

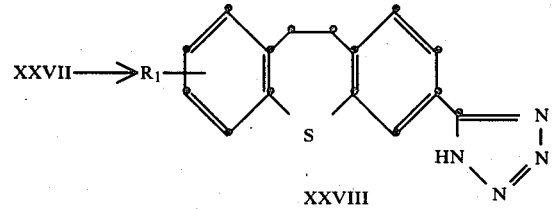

XXVIII

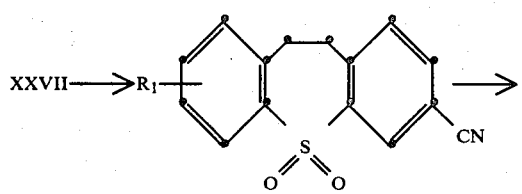

XXIX

Tetrazole XXVIII may be oxidized with peroxides such as hydrogen peroxide in acidic medium, such as acetic acid, to yield compound XXX.

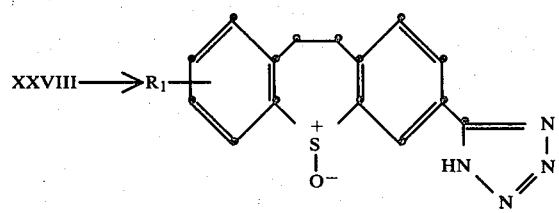

XXX

XVII may also be oxidized with one equivalent of organic peroxide, such as peroxy acids, for example, m-chloroperbenzoic acid followed by mineral acid or base hydrolysis to yield XXXI.

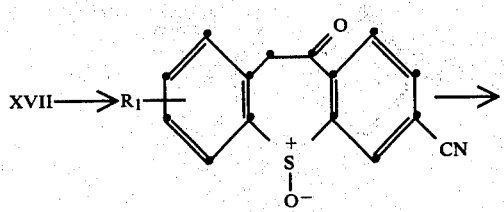

XVII

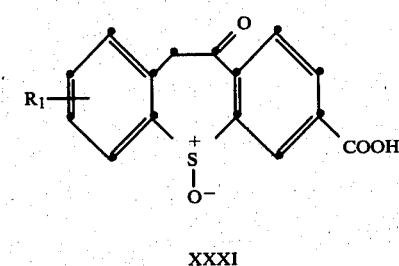

XXXI

XVII can also be reacted with azide ion at reflux in an inert solvent such as dimethylformamide or in THF with the addition of a Lewis acid such as AlCl₃ to yield the tetrazole XXXII.

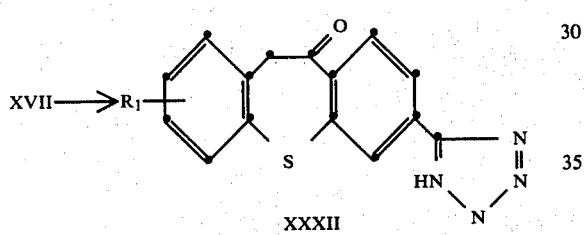

XXXII

Substituent R in I can also be introduced by modification of the nitro group in VIII (R=NO₂) and XXVII (R=NO₂) by known procedures. For example, XXXIII can be reduced with stannous chloride in acidic medium, hydrochloric acid and the like, to yield XXIV which can be hydrolyzed with mineral acids or bases to XXXV.

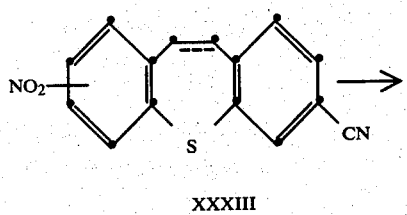

XXXIII

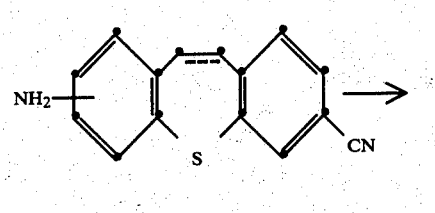

XXXIV

-continued

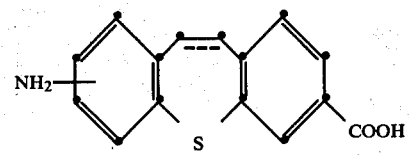

XXXV

Alternatively, XXXIII may be oxidized with peroxides, for example, m-chloroperbenzoic acid to yield XXXVI which can be reduced to XXXVII and then hydrolyzed with mineral acids or bases to XXXVIII.

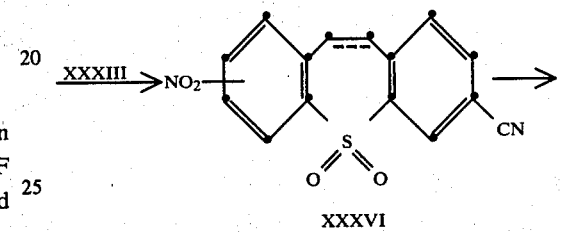

XXXVI

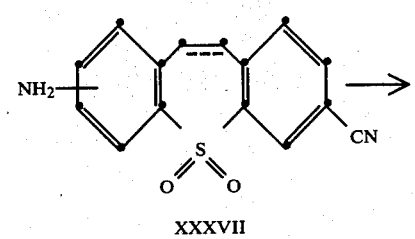

XXXVII

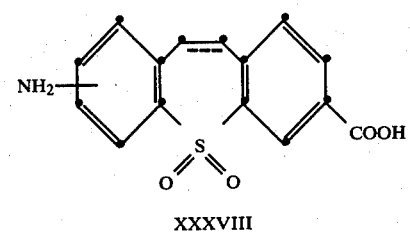

XXXVIII

Intermediate XXXIV can be reacted with sodium nitrite in mineral acid to the diazonium salt XXXIX, where X is a mineral acid counter ion, for example, Cl⁻, HSO₄⁻, BF₄⁻ and the like, which on reaction with CuCl and CuCl₂ yields intermediate XL which can be hydrolyzed to the acid XLI. Intermediate XL may also be oxidized to the sulfone derivative, then followed by a hydrolysis to the carboxylic acid XLII.

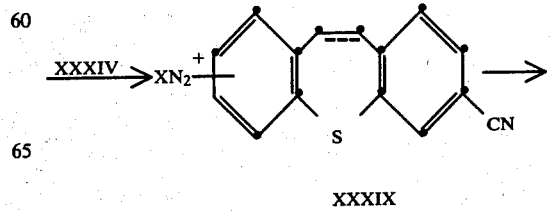

XXXIX

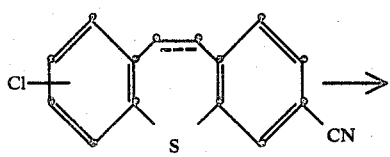
XL

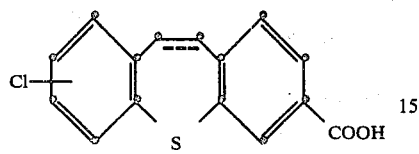
XLI

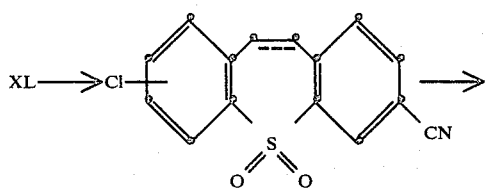
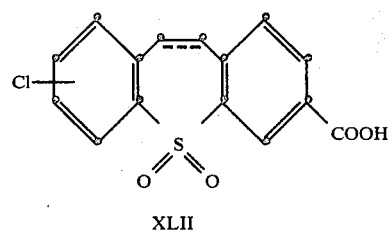
XLII

Derivative XXXIX can be hydrolyzed with a solution of sulfuric acid 10 to 50% in strength at temperatures ranging from 0°–90° C. to yield XLIII. XXXIX may also be reacted with potassium thioxanthate at temperatures from 40°–70° C. followed by basic hydrolysis to yield the thiol acid XLIV.

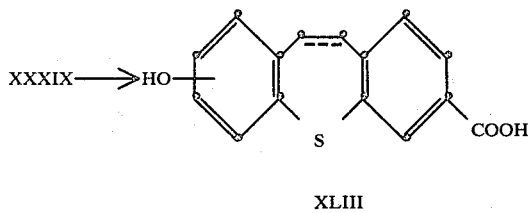
XLIII

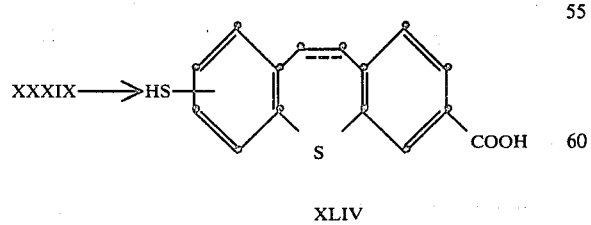
XLIV

Compound XXXVII can be transformed in the usual manner to the diazonium salt XLV. XLV can be reacted as described above to yield compounds XLVI AND XLVII.

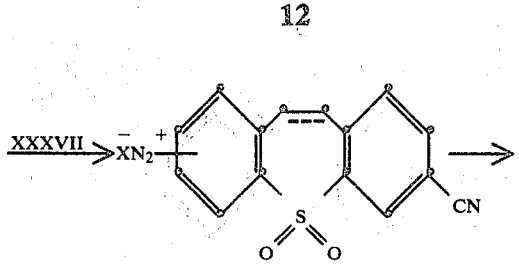
XLV

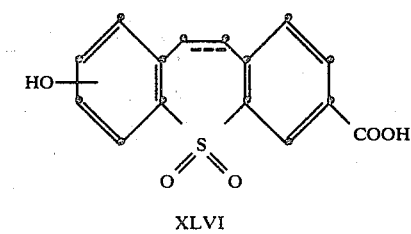
XLVI

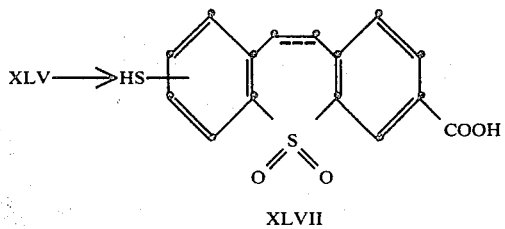
XLVII

Compounds XLIII, XLIV, XLVI, XLVII can be reacted with alkyl halides RX in which R is a lower alkyl $C_1$ to $C_4$, benzyl, and X is a leaving group such as Cl, Br, I,

in the presence of bases such as alkali carbonate, hydroxides, and the like, in solvents such as dimethylformamide, at temperatures ranging from 30°–160° C. to yield XLVIII, XLIX, L and LI, respectively.

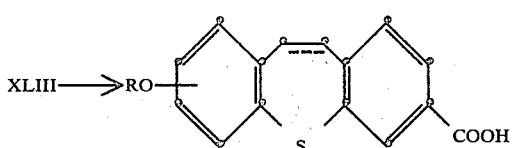
XLVIII

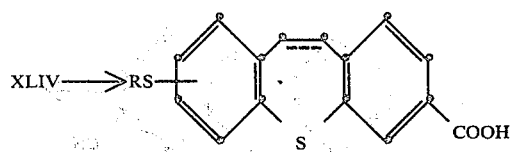
XLIX

-continued

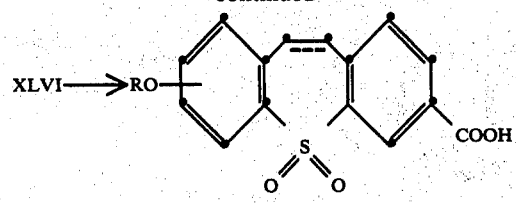

L

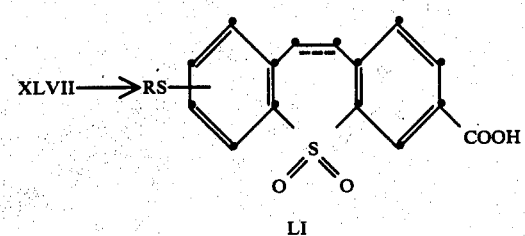

LI

Compound XLIX can in a controlled oxidation with peroxides such as hydrogen peroxide or organic peroxy acids such as m-chloroperbenzoic acid, yield compound LII. LI may be oxidized with one equivalent of organic peroxides such as m-chloroperbenzoic acid or with hydrogen peroxide in hydroxylic solvents such as alcohols, organic acids such as acetic acid, at temperatures below 30° C., to yield LIII. Compounds XLIX, LI and LIII may also be oxidized with excess organic peroxides such as m-chloroperbenzoic acid at room temperature, or with peroxides such as hydrogen peroxide in acidic medium such as acetic acid at temperatures between 80° and 100° C. to yield LIV.

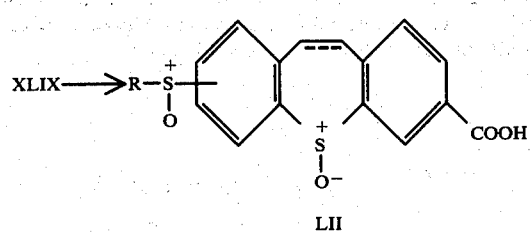

LII

-continued

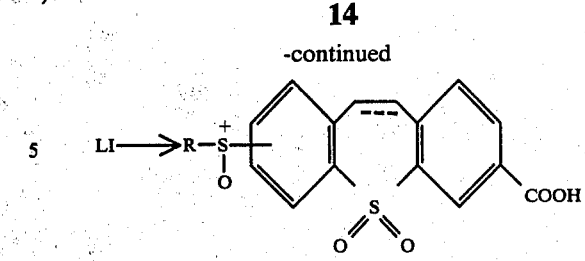

LIII

XLIX, LI, LIII ⟶

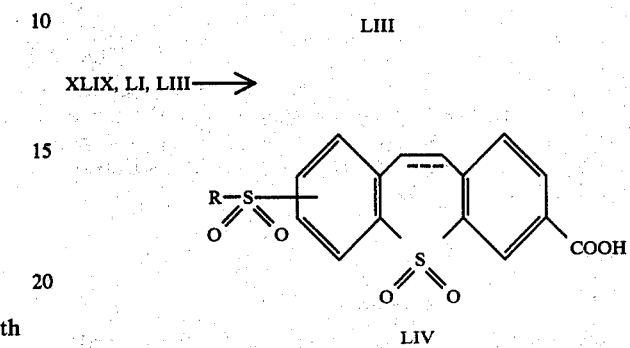

LIV

Specific introduction of substituents in position 8 in I can also be achieved. For example, XXVII ($R_1 = H$) can react with alkanoyl halide RCOX or alkanoic anhydride RCOOCOR in which R is a lower alkyl $C_1$ to $C_4$ and X is chloro or bromo, to yield the substituted acyl LV which upon acid or base hydrolysis affords acid LVI.

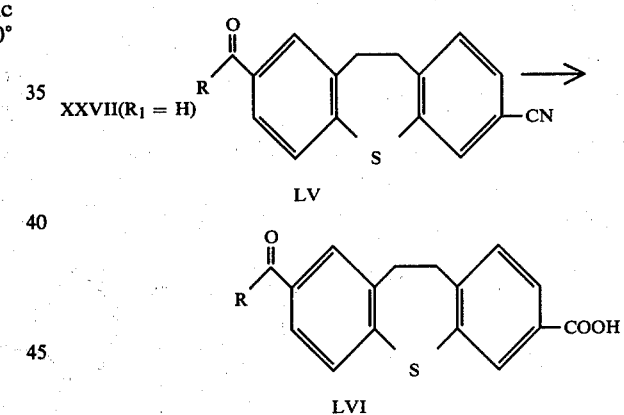

LV

LVI

Lv can be oxidized with oxidizing agents such as in-chloro perbenzoic acid stepwise to yield sulfoxide LVII and LVIII which are hydrolyzed under acidic or basic conditions to afford acids LIX and LX respectively.

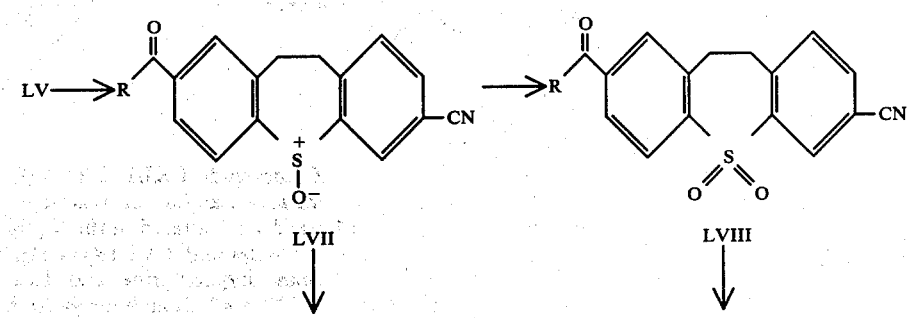

LVII   LVIII

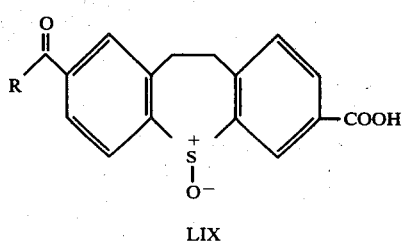

LIX

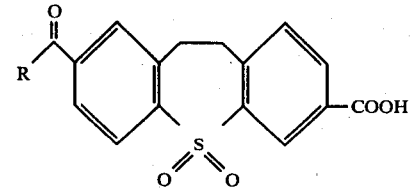

LX

Compound LVI can be reacted with hydroxylamide hydro chloride with presence of base to yield oxime LXI which on a Beckman rearrangement, yields the acylamino compound LXII which upon hydrolysis yields amino acid LXIII.

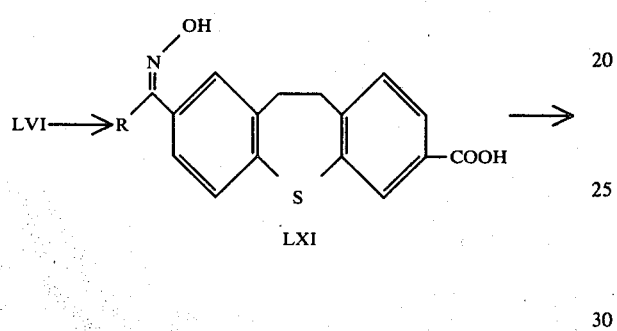

LVI ⟶ LXI

-continued

LXII

LXIII

Compound LXII can be oxidized with hydrogen peroxide in acetic acid stepwise to yield the corresponding sulfoxide LXIV and sulfone LXV which upon hydrolysis afford the acids LXVI and LXVII.

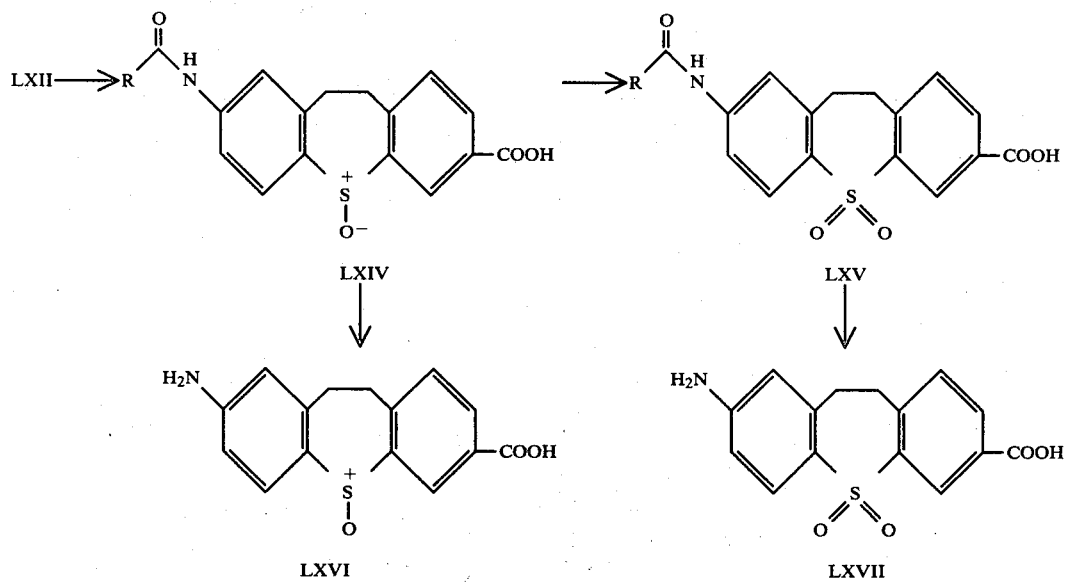

LXII ⟶ LXIV ⟶ LXVI

LXV ⟶ LXVII

Compounds LXIII, LXVI, LXVII can be treated in various Sandmeyer reactions as described earlier to yield I substituted in the 8 position.

Compound LVI (R=CH₃) when treated with sodium hypochloride and base at temperatures from 0°–70° for half an hour yield the diacid LXVIII. When the process is carried for 2 days under the same condition LXIX is obtained.

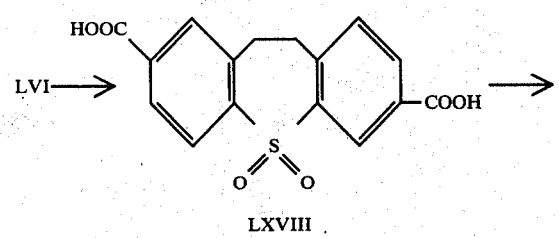

LXVIII

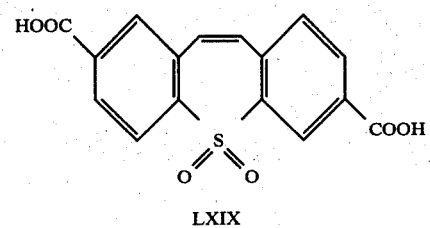

LXIX

Compounds LVI, LIX, LX can be reduced with sodium borohydrid to afford the corresponding alcohols, LXX, LXXI, LXXII.

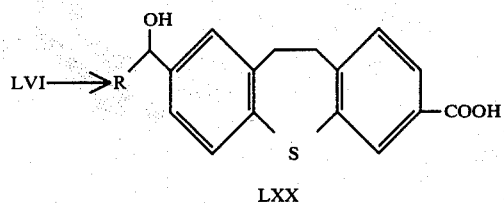

LXX

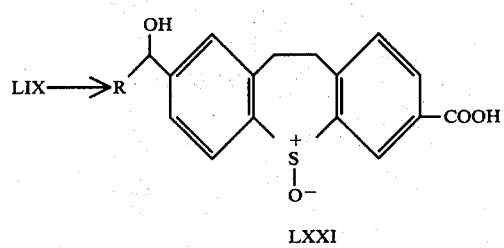

LXXI

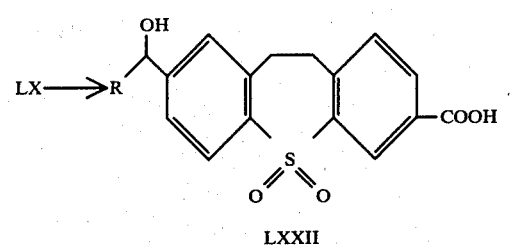

LXXII

It will be obvious to those skilled in the art that the nitrile, XVII, can be substituted for the nitrile starting material, XXVII, in the foregoing reaction sequences in order to prepare correspondingly substituted 10,11-dihydro-11-oxodibenzo [b,f]thiepins.

In addition to their therapeutic properties as noted above, the 3-carboxylic acid derivatives of this invention serve as valuable intermediates in the preparation of other variously substituted thiepins of formula I. Thus, for example, the 3-carboxylic acid of formula XVIII ($R_1=R$ as defined in formula I) may be converted readily into the corresponding acid halide, preferably the acid chloride, by treating the carboxylic acid with a thionyl halide, preferably thionyl chloride. The resulting 3-halocarbonyl 10,11-dihydro-11-oxodibenz[b,f][1,4]thiepin i.e., the 3-chlorocarbonyl compound of formula LXXIII then may be treated with various well-known reagents to form desired ester and amide derivatives. These reactions are illustrated in the following reaction scheme wherein R is as previously defined, it being understood that they are equally applicable to the 3-carboxylic acids of formula IX or XXIII.

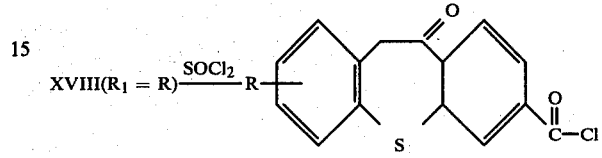

LXXIII

Thus, for example, the chlorocarbonyl compound of formula LXXIII may be treated:

(a) with a loweralkanol such as, for example, methanol, ethanol, 2-propanol, butanol and 2-butanol, to form the corresponding loweralkyl ester, LXXIV:

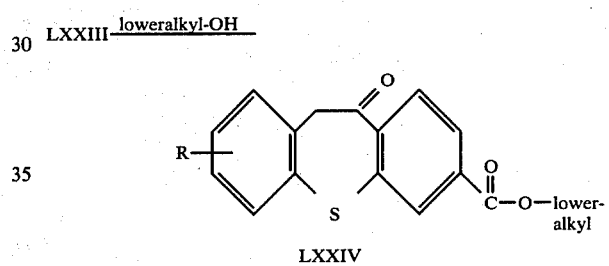

LXXIV (b) with ammonia to form the corresponding carboxamide, LXXV:

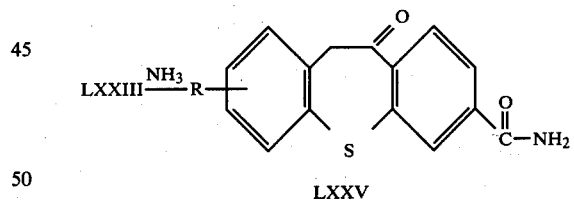

LXXV (c) with an N-loweralkylamine such as for example, methylamine, ethylamine, propylamine, isopropylamine and butylamine, or an N,N-diloweralkylamine such as, for example, dimethylamine, diethylamine, dipropylamine and dibutylamine, to form the corresponding N-loweralkylcarboxamide LXXVI or N,N-diloweralkylcarboxamide, LXXVII:

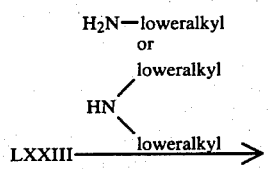

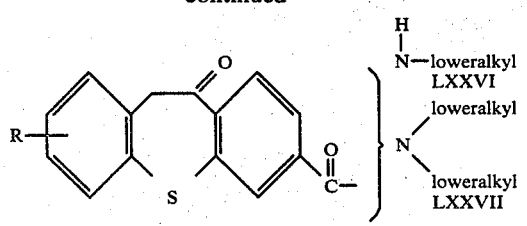

(d) with a loweralkylsulphonamide such as, for example, methane sulphonamide, ethane sulphonamide, propane sulphonamide and butane sulphonamide, to form the corresponding N-loweralkylsulfonylcarboxamide, LXXVIII:

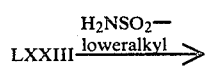

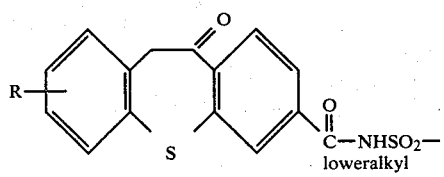

(e) with 2-imino-3-methylthiazolidine to form the corresponding (3-methyl-2-thiazolidinylidene)carboxamide, LXXIX:

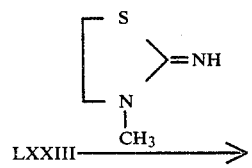

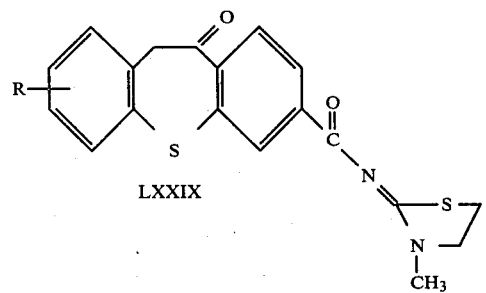

(f) with a loweralkyldiol such as, for example ethylene glycol, trimethylene glycol and 1,4-butanediol, to form the corresponding hydroxyloweralkylester, LXXX:

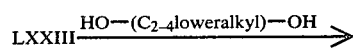

(g) with an N,N-diloweralkylaminoloweralkanol such as, for example, N,N dimethylethanolamine, N,N-diethylethanolamine, 3-N,N-dimethylaminopropan-1-ol and 4-N,N-diethylaminobutan-1-ol, to form the corresponding N,N-diloweralkylaminoloweralkyl ester, LXXXI:

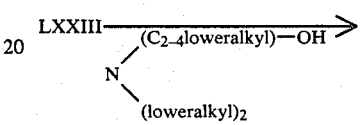

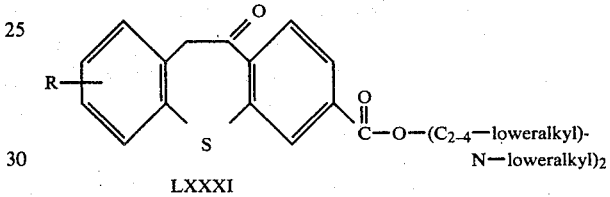

(h) with an amino acid such as, for example, glycine, alanine and valine, to form the corresponding N-carboxyloweralkylcarboxamide, LXXXII:

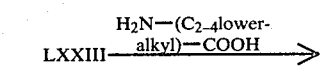

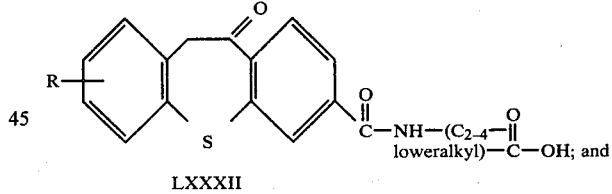

(i) with an alkali metal salt of a hydroxyloweralkanoic acid such as, for example, hydroxyacetic acid, 3-hydroxybutyric acid and β-hydroxypropionic acid, to form the corresponding carboxyloweralkyl ester, LXXXIII:

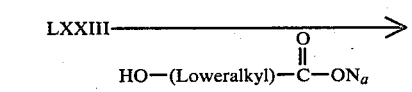

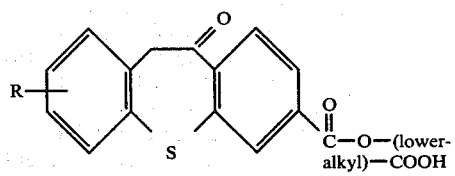

Where the corresponding sulfinyl or sulfonyl derivatives are desired, the corresponding 11-oxide or 11,11-dioxide 3-carboxylic acid may be substituted for starting material XVIII in the foregoing reaction sequence. Alternatively, it will be clear to those skilled in the art that the product esters and amides obtained in the foregoing reaction sequence may be oxidized by the techniques already described to obtain the corresponding sulfinyl or sulfonyl derivatives.

Those thiepins of this invention wherein the substituent at the 3-position is 3-hydroxyl-1,2,5-thiadiazol-4-yl are prepared by refluxing a 3-cyano intermediate (a compound of formula XVII where $R_1 = R$ as defined in formula I, for example) in formic acid in the presence of Raney nickel alloy for 1 to 2 hours in order to obtain the corresponding 10,11-dihydro-11-oxodibenzo-[b,f]-thiepin-3-carboxaldehyde. The aldehyde product then is converted into the corresponding 3-(2-aminoacetonitrile) by treatment with sodium cyanide in an alcoholic solvent saturated with ammonia and in the presence of ammonium chloride and ammonium hydroxide. The reaction usually is conducted at room temperature and requires from 8 to 16 hours for completion. The aminoacetonitrile so produced is treated with concentrated hydrochloric acid at room temperature for 20 to 45 minutes in order to obtain the corresponding 3-(2-aminoacetamide) which then is treated with sulfur monochloride in dimethylformamide to obtain the desired 10,11-dihydro-11-oxo-dibenzo[b,f]-thiepin-3-(3-hydroxy-1,2,5-thiadiazol-4-yl) of formula LXXXIV. This reaction sequence is illustrated in the following diagram.

2 to 4 hours for completion. The alcohol then is brominated with phosphorous tribromide and the bromomethyl compound so produced is treated with sodium cyanide to form the corresponding 3-cyanomethyl derivative. These reactions may be carried out at room temperature and usually require from 1 to 3 hours for completion. The cyanomethyl intermediate then is hydrolyzed to the corresponding acetic acid which is treated with thionyl chloride followed by ammonia to form the corresponding 3-acetamide derivative by techniques already described. The acetamide then is treated with diethyloxalate in dimethylformamide in the presence of potassium t-butoxide to form the desired dibenzo[b,f]thiepin-3-(4-hydroxy-$\Delta^3$-pyrrolin-3-yl-2,5-dione), LXXXV. This reaction sequence is illustrated in the diagram below.

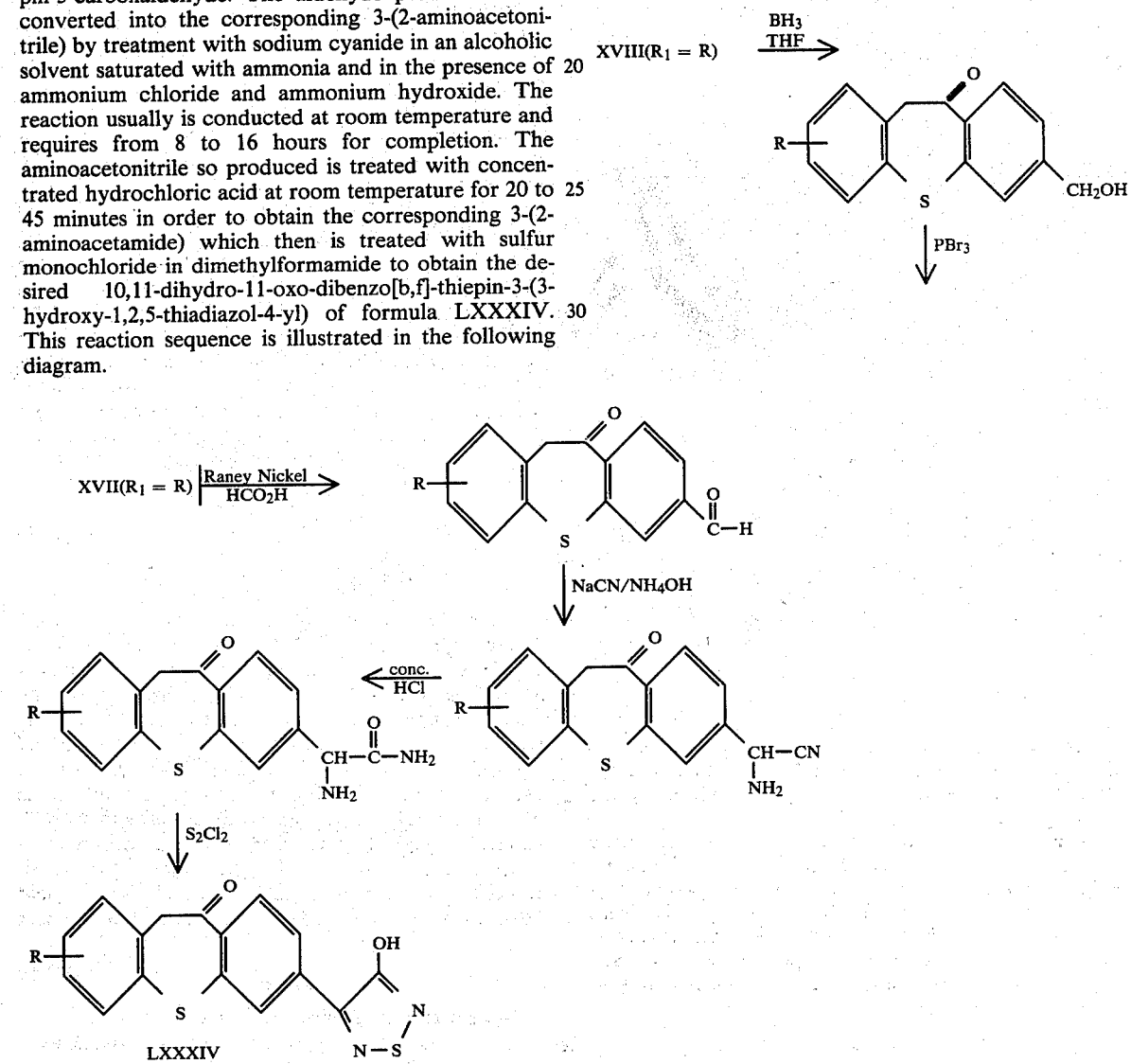

The novel thiepins of this invention wherein the substituent at the 3-position is 4-hydroxy-$\Delta^3$-pyrroline-3-yl-2,5-dione are prepared from the appropriately substituted 3-carboxylic acid by reducing the acid to the corresponding alcohol with borane in tetrahydrofuran. The reaction conveniently is carried out at room temperature under an inert atmosphere and usually requires

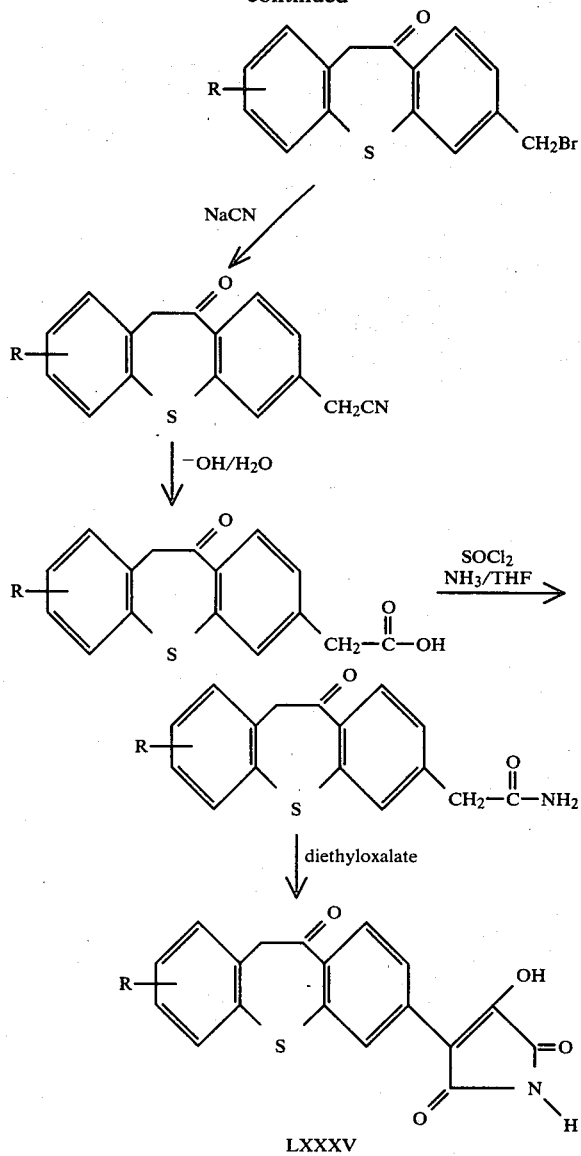

LXXXV

Where corresponding sulfinyl or sulfonyl derivatives are desired, the products of the four reaction schemes described immediately above may be oxidized by the techniques already described.

It will be noted that the reaction sequence described above affords not only thiepins of this invention wherein the substituent at the 3-position is 4-hydroxy-$\Delta^3$-pyrroline-3-yl-2,5-dione, but, in Steps A-D, leads also to the preparation of those thiepins of this invention wherein the substituent at the 3-position is a loweralkanoic acid (i.e., compounds of formula I wherein A is

n is an integer between 1 and 4 and $R_2$ is hydroxy). Thus, Steps A-D, as described above, starting with the appropriately substituted 3-carboxylic acid, through reduction, bromination, cyanization and oxidation, affords the corresponding 3-acetic acid derivative. Quite obviously, the described reduction, bromination, cyanization and oxidation sequence can be repeated, employing the 3-acetic acid derivative as starting material, in order to obtain the corresponding propionic acid derivative which, in turn, can be employed as starting material for preparing the corresponding butyric acid derivative. In this manner, any desired 3-loweralkanoic acid derivative of the instant invention readily is prepared. Corresponding sulfinyl or sulfonyl derivatives are prepared by the oxidation techniques previously described.

The 3-cyanoloweralkyl intermediates obtained from Steps A-C in the reaction sequence described above also serve as intermediates in the preparation of other therapeutically active thiepins of formula I. Thus, for example, an appropriately substituted 3—cyanomethyl-10,11-oxodibenzo[b,f]thiepin may be treated with sodium azide and ammonia by techniques previously described to form the corresponding 3-(1H-tetrazol-5-ylmethyl)-10,11-dihydro-11-oxodibenzo[b,f]thiepin and the product, if desired, can be oxidized to form the corresponding sulfinyl or sulfonyl derivative.

As noted above, pharmaceutically acceptable salts of the novel thiepins also are included within the scope of this invention. The term, pharmaceutically acceptable salts, is intended to include salts derived from pharmaceutically acceptable non-toxic acids and bases such as, for example, ammonium salts, alkali metal salts such as sodium and potassium salts, alkaline earth metal salts such as magnesium and calcium salts, salts or organic bases such as amine salts derived from mono-, di and tri-loweralkyl or loweralkanoyl amines such as trimethylamine, dimethylamine and triethanolamine, salts derived from heterocyclic amines such as piperidine, pyridine, piperazine and morpholine, and salts derived from pharmaceutically acceptable acids such as hydrochloric acid, sulfuric acid, tartaric acid and propionic acid.

EXAMPLE I

STEP 1

2-(3-Bromophenylthio)benzoic Acid

A mixture consisting of 179 g. m-dibromobenzene (0.758 mole); 46.6 g. thiosalicyclic acid (0.303 mole); 25.9 g cuprous oxide (0.181 mole); 212 cc. quinoline; and 24 cc. pyridine is mechanically stirred and heated in an oil bath at 200° C. to 210° C. for three hours. The internal temperature remains constant at 145° C. The reaction mixture is then poured into 1500 cc. of 5N aqueous HCl. The oily solid is filtered, then dissolved in 750 cc. 1N aqueous NaOH solution; this solution is filtered through celite, then extracted three times with ether. The aqueous fraction is acidified with concentrated HCl and the resulting grayish solid filtered, washed well with water and dried. The crude yield obtained is 65 g. (69.4%). It is used as such in the next step.

STEP 2

2-(3-Bromophenylthio)benzyl Alcohol

A solution of 63.3 g. of 2-(3-bromophenylthio)benzoic acid (0.205 mole, crude) in 400 cc. dry tetrahydrofuran (THF) is treated dropwise at room temperature and under nitrogen atmosphere with 240 cc. 0.96 N borane in THF. Hydrogen evolution is noticed during approximately one-third of the addition. After completion of the addition, the mixture is left stirring for one additional hour, then decomposed by the dropwise addition of 15 cc. water. Most of the THF is evaporated off and the residue is partitioned ether and water. The organic phase contains the crude alcohol which is chromatographed on a column of silica gel (1 kg.); elution is done with a mixture of 20% ethyl acetate in benzene. Pure 2-(3-bromophenylthio)-3-nitrobenzyl alcohol (50.03 g.) is obtained as a yellow oil (82.8% yield).

STEP 3

2-(3-Bromophenylthio)benzyl Bromide

To 50.03 g. 2-(3-bromophenylthio)benzyl alcohol (0.17 mole) cooled in an ice bath is added dropwise 6 cc. phosphorous tribromide (0.06 mole). The resulting milky oil is stirred in the cold an additional 15 minutes then decomposed with ice water. Extraction with ether affords 58.6 g. of 2-(3-bromophenylthio)benzyl bromide as a yellowish-brown oil which is used as such in the next step.

STEP 4

2-(3-Bromophenylthio)benzyl Cyanide 12.4 G. sodium cyanide (0.25 mole) is added to the solution of 58.6 g. 2-(3-bromophenylthio)benzyl bromide (0.164 mole) in 200 cc. dimethylformamide (DMF). The reaction is slightly exothermic. The resulting solution is allowed to stir for an hour without cooling, then is diluted with a large volume of water and extracted with ether three times. Ether extracts are washed several times with water, dried over sodium sulfate and the ether evaporated off. The crude yield of 2-(3-bromophenylthio)benzyl cyanide is 49.6 g.; the product is an oil which is hydrolyzed as such.

STEP 5

2-(3:Bromophenylthio)benzyl Acetic Acid 49.6 G. crude 2-(3-bromophenythio)benzyl cyanide is refluxed in a mixture of 650 cc. 20% aqueous sodium hydroxide solution and 650 cc. denatured alcohol for three hours. The solution is concentrated and the sodium salt of the acid separates. The mixture is diluted to three liters with water and acidified with concentrated HCl. The free acid precipitates and is filtered. The yield of crude 2-(3-bromophenylthio)phenyl acetic acid is 49.3 g. (93.5%). It is used as such in the next step.

STEP 6

3-Bromo-10,11-dihydro-11-oxodibenzo[b,f]thiepin 49.3 G. (0.1526 mole) crude 2-(3-bromophenylthio)-phenyl acetic acid and 50 cc. thionyl chloride are refluxed together for 10 minutes. The excess thionyl chloride is evaporated off and the residual oil dissolved in 1,2-dichloroethane and the mixture evaporated again to remove the last traces of thionyl chloride.

The oily acid chloride is dissolved in 400 cc. 1,2-dichloroethane and 22.4 g. aluminum chloride (10% excess) is added in portions. The reaction is slightly exothermic but no cooling is necessary. The reaction is permitted to go for 40 minutes then the mixture is poured onto ice. The organic fraction is collected and the aqueous fraction extracted three times with chloroform. Combined organics are washed with water, dried over sodium sulfate and stripped to dryness. The solid residue is triturated in ether and filtered, then triturated in methanol and filtered. The yield of crude product is 34.8 g. (74.8%).

STEP 7

3-Bromo-10,11-dihydro-11-hydroxydibenzo[b,f]thiepin

17 G. of 3-bromo-10,11-dihydro-11-oxodibenzo[b,f]thiepin (0.056 mole) are dissolved in a mixture of 150 cc. DMF and 150 cc. absolute alcohol. 1.7 G. sodium borohydride (0.045 mole) are added and the mixture is left stirring overnight at room temperature. The ethanol is evaporated and the residual DMF solution is diluted with water and extracted with ether three times. The ether extracts are washed several times with water, dried and evaporated to a thick oil. A quantitative yield of the alcohol is obtained.

STEP 8

3-Bromodibenzo[b,f]thiepin

17 G. 3-bromo-11-hydroxy-10,11-dihydrodibenzo[b,f]thiepin are dissolved in 600 cc. benzene; 1 gram p-toluene sulfonic acid is added and the mixture is refluxed with elimination of water for two hours. The solution is cooled and washed with aqueous sodium bicarbonate solution and water, dried and stripped to a solid residue. 16 G. of 3-bromodibenzo[b,f]thiepin are obtained.

STEP 9

3-Cyanodibenzo[b,f]thiepin

A mixture containing 15.4 g. 3-bromodibenzo[b,f]thiepin and 7.16 g. cuprous cyanide (50% excess) in 100 cc. DMF is refluxed for 10 hours. The dark mixture is cooled in 10° C. and poured onto 500 cc. 20% aqueous HCl solution. Solids are filtered and washed well with water, then dissolved in chloroform. The solution is filtered through celite to remove insoluble cuprous salts, then evaporated to a solid residue. Chromatography on silica gel, eluting with benzene, affords 7.3 g. pure 3-cyanodibenzo[b,f]thiepin as a yellow solid, m.p. 108° C.–110° C. Yield is 58.3%.

STEP 10

Dibenzo[b,f]thiepin-3-carboxylic Acid 2.0 G. 3-cyanodibenzo[b,f]thiepin are refluxed in a mixture of 25 cc. concentrated HCl and 25 cc. glacial acetic acid for 19 hours; the acid separates from the hot solution. After cooling, the mixture is diluted with water and the light yellow solid is filtered and washed well with water. The yield of dibenzo[b,f]thiepin-3-carboxylic acid is 2.07 g. (95.8%), m.p. 251° C.–254° C.

Calculated: C: 70.85; H: 3.95; S: 12.61.

Found: C: 71.05; H: 3.88; S: 12.35.

EXAMPLE II

STEP 1

3-Cyanodibenzo[b,f]thiepin-5-oxide

5 G. 3-cyanodibenzo[b,f]thiepin (0.021 mole) are dissolved in 300 cc. methylene chloride and 3.45 g. m-chloroperbenzoic acid (0.020 mole) are added in portions. The solution is stirred for two hours at room temperature, then excess calcium hydroxide is added. The mixture is stirred for a few minutes and filtered through celite, the filtrate is evaporated down and the residue chromatographed on silica gel, eluting with a 50:50 mixture of chloroform and benzene. A small amount of starting material is recovered, and the yield of sulfoxide is 4.92 g. (92%), light yellow solid, m.p. 220° C.–222° C.

STEP 2

Dibenzo[b,f]thiepin-3-carboxylic Acid 5-Oxide

925 Mg. 3-cyanodibenzo[b,f]thiepin 5-oxide are refluxed for 3½ hours in a mixture of 60 cc. 10% aqueous sodium hydroxide solution and 60 cc. denatured alcohol. The mixture is diluted with ½ liter of water and acidified with concentrated HCl. The acid precipitates and is filtered and dried. The yield of white dibenzo[b,f]thiepin-3-carboxylic acid 5-oxide is 965 mg. (97%), m.p. dec. 249° C.

Calculated: C: 66.75; H: 3.73; S: 11.86. Found: C: 66.75; H: 3.62; S: 11.67.

EXAMPLE III

STEP 1

3-Cyanodibenzo[b,f]thiepin-5,5-dioxide 5.4 G. 3-cyanodibenzo[b,f]thiepin (0.023 mole) are dissolved in 300 cc. methylene chloride and 15.87 g. m-chlorperbenzoic acid (0.092 mole) are added in portions. The resulting solution is stirred at room temperature for one hour, then excess calcium hydroxide is added. The mixture is filtered through celite and the filtrate is stripped to dryness. The yellow solid is triturated in benzene and filtered. One obtains 5.46 g. (89%) of the sulfone, m.p. 229° C.–231° C.

STEP 2

Dibenzo[b,f]thiepin-3-carboxylic Acid 5,5-Dioxide 13.6 G. 3-cyanodibenzo[b,f]thiepin-5,5-dioxide are refluxed for 2.5 hours in a mixture of 20 cc. 10% aqueous sodium hydroxide solution and 20 cc. ethanol. The mixture is diluted with water and acidified with concentrated HCl. The acid precipitates as a white solid. The yield of acid, m.p. 268° C.–270° C. is 1.38 g. (94.6%).

Calculated: C: 62.93; H: 3.52; S: 11.20. Found: C: 62.72; H: 3.58; S: 10.91.

EXAMPLE IV 3-(5-Tetrazolyl)dibenzo[b,f]thiepin 5,5-Dioxide
A mixture made up of:
1 g. 3-cyanodibenzo[b,f]thiepin 5,5-dioxide (3.75 millimoles);
302 mg. sodium azide (4.65 millimoles);
273 mg. ammonium chloride (5.10 millimoles);
20 cc. DMF is refluxed for 16 hours.

After cooling, the mixture is diluted with 10% aqueous sodium carbonate solution; the resulting solution is extracted three times with ether, thus affording 302 mg. recovered starting material. The aqueous fraction is acidified with concentrated HCl and the crude tetrazole (700 mg.) is filtered. It is chromatographed on a column of silica gel, eluting with a solvent mixture consisting of 4 parts methanol, 10 parts chloroform, 1 part 28% aqueous ammonium hydroxide. The product is obtained from the column as the ammonium salt; it is dissolved in water and the solution is washed with chloroform. The aqueous fraction is then acidified with aqueous HCl solution and the tetrazole precipitates and is filtered and dried. The yield is 350 mg. (30%) of yellowish solid, m.p., dec. 247° C.

Calculated: C: 58.06; H: 3.25; N: 18.05; S: 10.32. Found: C: 58.29; H: 3.08; N: 18.17; S: 10.11.

EXAMPLE V 3-(5-Tetrazolyl)dibenzo[b,f]thiepin
A mixture consisting of 4 g. 3-cyanodibenzo[b,f]thiepin (17 millimoles); 1.8 g. sodium azide (28 millimoles); 1.63 g. ammonium chloride (30.5 millimoles) and 50 cc. DMF is refluxed for 17 hours. The mixture is cooled and diluted with aqueous sodium carbonate solution. The solution is extracted with ether, then acidified with aqueous HCl solution. The tetrazole precipitates and is filtered. Crystallization from methanol affords 3.93 g. (83%) yellow product, m.p., 213° C.–214° C.

Calculated: C: 64.75; H: 3.59; N: 20.14; S: 11.51. Found: C: 65.03; H: 3.71; N: 19.94; S: 11.74.

EXAMPLE VI 3-(5-Tetrazolyl)dibenzo[b,f]thiepin-5-oxide

To a solution of 2.03 g. (7.3 millimoles) of 3-(5-tetrazolyl)dibenzo[b,f]thiepin in 100 cc. glacial acetic acid is added 15 cc. 30% aqueous hydrogen peroxide. The mixture is heated to 65° C. for 10 minutes; the sulfoxide separates from the hot solution. After cooling and diluting with water, the crystalline product is filtered and washed with water. It is then heated on a steam bath in 25 cc. DMF and filtered hot. The solid is washed with methanol and dried. The yield of sulfoxide is 1.55 g. (72%) as a white solid decomposing at 277° C.–279° C.

Calculated: C: 61.21; H: 3.40; N: 19.03; S: 10.09. Found: C: 60.93; H: 3.41; N: 19.08; S: 10.66.

EXAMPLE VII

STEP 1

3-Cyano-10,11-dihydro-11-oxodibenzo[b,f]thiepin 36.45 G. 3-bromo-10,11-dihydro-11-oxodibenzo[b,f]thiepin and 32.11 g. cuprous cyanide are refluxed in 450 cc. dimethylformamide for five and one half hours. The reaction mixture is cooled down and poured into 2 l. of ice water with good mechanical stirring. The resulting solid is filtered, washed with water, then extracted into 1.7 l. chloroform. The insoluble copper salts are filtered and the filtrate evaporated to dryness. The residue is triturated in methanol and the insoluble yellow product is filtered and weighs 22.4 g. (74.6%), m.p. 166°–170° C.

STEP 2

10,11-Dihydro-11-oxodibenzo[b,f]thiepin-3-carboxylic Acid

20 G. of 3-cyano-1-,11-dihydro-11-oxodibenzo[b,f]thiepin are refluxed in a mixture of 200 cc. concentrated hydrochloric acid and 200 cc. acetic acid for 21 hours. The desired acid precipitates out of the solution and is filtered while hot and washed with water and dried to yield 17.3 g. light yellow solid. From the mother liquors 2.74 g. of additional material are recovered, total yield 93.6%.

STEP 3

10,11-Dihydro-11-hydroxydibenzo[b,f]thiepin-3-carboxylic Acid 16.3 G. 10,11-dihydro-11-oxodibenzo[b,f]thiepin-3-carboxylic acid is stirred in aqueous sodium bicarbonate solution and 5 g. sodium borohydride is added in portions. The foaming mixture is stirred for an additional half hour. The solution is extracted with ether and the aqueous layer acidified with hydrochloric acid and the solid filtered and dried to yield 15.8 g. of the desired yellow solid (96.2% yield), m.p. 202°–204° C.

Calculated: C: 66.16; H: 4.44; S: 11.77. Found: C: 66.00; H: 4.62; S: 11.54.

STEP 4

Methyl-10,11-dihydro-11-hydroxydibenzo[b,f]thiepin-3-carboxylate 13.5 G. 10,11-dihydro-11-hydroxydibenzo[b,f]thiepin-3-carboxylic acid is suspended in ether and excess diazomethane is added in portions. A clear solution results which is filtered from small particles in suspension and the filtrate evaporated to dryness to a yellow oil weighing 14.2 g.

STEP 5

Methyl 11-bromo-10,11-dihydrodibenzo[b,f]thiepin-3-carboxylate 14.7 G. methyl-10,11-dihydro-11-hydroxydibenzo[b,f]thiepin-3-carboxylate are dissolved in 400 cc. ether and 5 cc. phosphorous tribromide is added. The mixture is stirred at room temperature for 15 minutes. Ice is added and the mixture is filtered to yield a first crop of material. The organic layer in the filtrate is separated, dried and evaporated; the residue triturated with ether and filtered affords a second crop. The two crops are combined and dried to yield 15.47 g., m.p. 116°–123° C.

STEP 6

Methyl-10,11-dihydrodibenzo[b,f]thiepin-3-carboxylate 13.6 G. methyl-11-bromo-10,11-dihydrodibenzo[b,f]thiepin-3-carboxylate is suspended in 150 cc. sulfolane and to the mechanically stirred mixture 7.18 g. sodium borohydride is added in portions over one hour. The foamy mixture is stirred an additional half hour. The mixture is diluted with 1.5 l. of water and extracted with ether. The organic layer is washed with water, dried, evaporated, and the residual oil is chromatographed on silica gel. Elution with benzene affords 8.1 g. of the pure oily material.

STEP 7

10,11-Dihydrodibenzo[b,f]thiepin-3-carboxylic Acid 5.6 G. methyl-10,11-dihydrodibenzo[b,f]thiepin-3-carboxylate is refluxed in a mixture of 50 cc. 20% aqueous sodium hydroxide and 50 cc. ethanol until a clear solution results (15 to 20 minutes). Most of the ethanol is evaporated away and aqueous residue is diluted with water and acidified with hydrochloric acid. The white solid is collected, recrystallized from acetic acid to yield 4.125 g. (77.7%) of the desired white crystalline material, m.p. 196°–198° C.

Calculated: C: 70.29; H: 4.72; S: 12.51. Found: C: 69.92; H: 4.71; S: 12.15.

EXAMPLE 8

STEP 1

Methyl 10,11-dihydrodibenzo[b,f]thiepin-3-carboxylate-5-oxide

540 Mg. methyl-10,11-dihydrodibenzo[b,f]thiepin-3-carboxylate is dissolved in 40 cc methylene chloride and m-chloroperbenzoic acid is added in small portions until TLC shows very little starting material left. Excess calcium hydroxide powder is added and the mixture filtered through celite. The organic layer is evaporated and the residue chromatographed on silica gel to afford 570 mg. (94.7%).

STEP 2

10,11-Dihydrodibenzo[b,f]thiepin-3-carboxylic Acid 5-oxide

520 Mg. methyl-10,11-dihydrodibenzo[b,f]thiepin-3-carboxylate 5-oxide is stirred at 65° C. in a mixture of 20 cc. 20% aqueous sodium hydroxide and 20 cc. ethanol until a clear solution results (1 hour). The mixture is diluted with water, extracted with ether, then acidified with hydrochloric acid. The white precipitate is filtered and dried to yield 245 mg. of material which is recrystallized from methanol to yield 180 mg., m.p. 261°–265° C.

EXAMPLE 9

10,11-Dihydrodibenzo[b,f]thiepin-3-carboxylic Acid 5,5-dioxide

735 Mg. of 10,11-dihydrodibenzo[b,f]thiepin-3-carboxylic acid is heated at 75°–80° C. in 30 cc. acetic acid and 5 cc. 30% hydrogen peroxide for 2 hours. The reaction mixture is cooled down, the crystals filtered and washed with water and dried to yield 650 mg., m.p. 248°–250° C.

Calculated: C: 62.49; H: 4.20; S: 11.12. Found: C: 62.1; H: 4.38; S: 10.97.

EXAMPLE 10

STEP 1

3,11-Dibromo-10,11-dihydrodibenzo[b,f]thiepin 10.5 G. 3-bromo-10,11-dihydro-11-hydroxydibenzo[b,f]thiepin and 25 cc. phosphorous tribromide are stirred for 2 hours, poured onto ice and extracted with ether. The ether is dried and evaporated to yield 10.65 g. of a brown oil which solifies on standing. The material is used as such for the next step.

STEP 2

3-Bromo-10,11-dihydrodibenzo[b,f]thiepin 10.55 G. 3,11-dibromo-10,11-dihydrodibenzo[b,f]thiepin is suspended in 150 cc. sulfolane and gradually, in portions, 3.5 g. sodium borohydride is added. When the foaming has subsided, water is added and the mixture extracted four times with ether, the combined extracts are washed several times with water, dried and evaporated to dryness, and the residual oil chromatographed on silica gel. On elution with 10% benzene in hexane, 3.31 g. of pure material as a white solid is obtained, m.p. 69°–71° C.

STEP 3

3-Cyano-10,11-dihydrodibenzo[b,f]thiepin 4.61 G. 3-bromo-10,11-dihydrodibenzo[b,f]thiepin and 4.3 g. cuprous cyanide are refluxed in 50 cc. dimethylformamide for 5½ hours. The mixture is poured onto ice and the solid filtered. The solid is triturated with chloroform and filtered. The chloroform is evaporated to yield 4.5 g. residue which is chromatographed on silica gel. Elution with benzene affords 2.83 g. (75.4%) of the desired pure oily compound which crystallizes on standing. Elution with ethyl acetate gives 440 mg. 10,11-dihydrodibenzo[b,f]thiepin-3-carboxylic acid amide as a white solid, m.p. 145°–147° C.

STEP 4

10,11-Dihydro-3-(5-tetrazolyl)dibenzo[b,f]thiepin

To 21 cc. dry tetrahydrofuran, cooled in an ice bath, 2.08 g. AlCl$_3$ is added, followed by 1.7 g. 3-cyano-10,11-dihydro[b,f]thiepin and 2.03 g. sodium azide. The resulting mixture is refluxed for 7 hours then cooled. 6.2 cc. 15% aqueous hydrochloric acid is added slowly. The reaction mixture is decanted, the residue extracted several times with ethyl acetate. The organics are combined, extracted several times with water, then once with sodium bicarbonate solution. The basic aqueous solution is acidified with hydrochloric acid. The tetrazole crystallizes out as white fluffy needles which are filtered and washed with water and dried, yield 1.065 g., m.p. 205° C.

Calculated: C:64.76; H: 4.31; N: 19.98; S: 11.44. Found: C: 64.13; H: 4.46; N: 19.87; S: 11.36.

EXAMPLE 11

10,11-Dihydro-3-(5-tetrazolyl)dibenzo[b,f]thiepin-5-oxide

A mixture of 600 mg. of 10,11-dihydro-3-(5-tetrazolyl)dibenzo[b,f]thiepin, 25 cc. acetic acid and 5 cc. 30% hydrogen peroxide is stirred for 6 hours. The suspended solid is filtered, washed with acetic acid, then water and dried to yield 575 mg. of pure material, m.p. 287° C. dec.

Calculated: C: 60.79; H: 4.08; N: 18.91; S: 10.82. Found: C: 60.65; H: 4.28; N: 18.77; S: 10.59.

EXAMPLE 12

STEP 1

3-Cyano-10,11-dihydrodibenzo[b,f]thiepin-5,5-dioxide

800 Mg. 3-cyano-10,11-dihydrodibenzo[b,f]thiepin is dissolved in 75 cc. methylene chloride and 1.73 g. m-chloroperbenzoic acid is added and the solution stirred at room temperature for three hours. An additional 10 cc. methylene chloride is added, followed by a large excess of powdered calcium hydroxide. After stirring for 5 minutes, the mixture is filtered through celite and the filtrate stripped to dryness and the residual solid triturated with ether and filtered to yield 854 mg. (94%) of the desired pure white solid.

STEP 2

10,11-Dihydro-3-(5-tetrazolyl)dibenzo[b,f]thiepin 5,5-dioxide

To 9 cc. tetrahydrofuran, cooled in an ice bath, is added in the following order 862 mg. aluminum chloride, 792 mg. 3-cyano-10,11-dihydrodibenzo[b,f]thiepin-5,5-dioxide, and 839 mg. sodium azide. The mixture is refluxed for six hours, cooled down, treated with 3 cc. 15% aqueous hydrochloric acid. The organic solvent is decanted and the residue triturated several times with ethyl acetate. The combined organic phases are washed with water, then extracted with aqueous sodium bicarbonate solution. The aqueous layer is acidified with hydrochloric acid and the precipitated tetrazole is filtered, washed with water, and dried, yield 580 mg. (63%), m.p. 233° C. dec.

Calculated: C: 57.68; H: 3.87; N: 17.94; S: 10.27. Found: C: 57.53; H: 4.06; N: 17.66; S: 10.15.

EXAMPLE 13

STEP 1

3-Cyano-10,11-dihydro-11-oxodibenzo[b,f]thiepin-5-oxide 1.63 G. 3-cyano-10,11-dihydro-11-oxodibenzo[b,f]thiepin is dissolved in 100 cc. methylene chloride and 1.12 g. m-chloroperbenzoic acid is added and the solution stirred for one hour at room temperature. The reaction mixture is diluted with methylene chloride, excess powdered calcium hydroxide is added, and the mixture stirred for five minutes and filtered through celite. The organic filtrate is evaporated to dryness and the residue chromatographed on silica gel and eluted with a 1:1 mixture of benzene: chloroform to yield 937 mg. (54%) of the desired pure sulfoxide, m.p. 219°–221° C.

STEP 2

10,11-Dihydro-11-oxodibenzo[b,f]thiepin-3-carboxylic Acid 5-oxide

780 Mg. 3-cyano-10,11-dihydro-11-oxodibenzo[b,f]thiepin 5-oxide is refluxed for four hours in a mixture of 50 cc. 10% aqueous sodium hydroxide and 50 cc. ethanol. The reaction mixture is diluted with water, acidified with hydrochloric acid, filtered and dried under vacuum in the oven at 70° C. The solid is recrystallized from a mixture of dimethylformamide and methanol to yield 360 mg. of the pure acid, m.p. 273° C. dec.

Calculated: C: 62.93; H: 3.52; S: 11.20. Found: C: 62.86; H: 3.77; S: 11.13.

EXAMPLE 14

10,11-Dihydro-11-oxo-3-(5-tetrazolyldibenzo[b,f]thiepin

To 25 cc. of freshly distilled tetrahydrofuran is added in the following order 2.35 g. aluminum chloride, 2 g. 3-cyano-10,11-dihydro-11-oxodibenzo[b,f]thiepin, and 2.3 g. sodium azide, and the mixture is refluxed for 8 hours, cooled and 7 cc. of 15% aqueous hydrochloric acid added. The supernatant layer is decanted and the residue triturated with ethyl acetate. The combined organic phases are extracted with aqueous sodium bicarbonate solution. The basic aqueous solution is acidified with hydrochloric acid and the solid filtered. After two recrystallizations from methanol, 850 mg. (36%) of the pure tetrazole is obtained, m.p. 235° C. dec.

Calculated: C: 61.21; H: b 3.42; N: 19.03; S: 10.89. Found: C: 60.92; H: 3.60; N: 18.76; S: 10.63.

EXAMPLE 15

STEP 1

2(3'-Bromophenylthio)-5-nitrobenzoic Acid

A mixture of 205 g. 3-bromothiophenol, 188 g. potassium hydroxide in 2 l. water, 205 g. 2-chloro-5-nitrobenzoic acid and 6.5 g. copper powder is refluxed for two hours, filtered while hot, acidified with hydrochloric acid and the solid filtered, washed with water and dried to yield 301 g. of the desired white solid, m.p. 202°–206° C.

STEP 2

2-(3'-Bromphenylthio)-5-nitrobenzyl Alcohol

Prepared in 83% yield as described in Example I, Step 2, m.p. 98°–101° C.

STEP 3

2-(3'-Bromophenylthio)-5-nitrobenzyl Bromide

Prepared in 96% yield as described in Example I, Step 3, m.p. 80°–82° C.

STEP 4

2-(3'-Bromophenylthio)-5-nitrobenzyl Cyanide 2.16 G. 2-(3'-bromophenylthio)-5-nitrobenzyl bromide is refluxed in 50 cc. ethanol and 2.4 g. of cyanide ion exchange resin for ½ hour. The mixture is filtered hot and the resin washed with ethyl acetate. The combined organic filtrates are evaporated to dryness to yield 1.85 g. of crude residue which is chromatographed on silica gel. Elution with benzene affords 800 mg. of the desired compound.

STEP 5

2-(3'-Bromophenylthio)-5-nitroacetic Acid 2-(3'-Bromophenylthio)-5-nitrobenzyl cyanide is hydrolyzed as described in Example I, Step 5, m.p. 123°–125° C.

STEP 6

3-Bromo-10,11-dihydro-8-nitro-11-oxodibenzo[b,f]-thiepin 2-(3'-Bromophenylthio)-5-nitroacetic acid is transformed to the title compound in 95% yield as described in Example I, Step 6, m.p. 242°–245° C.

STEP 7

3-Bromo-10,11-dihydro-11-hydroxy-8-nitrodibenzo[b,f]thiepin

3-Bromo-10,11-dihydro-8-nitro-11-oxodibenzo[b,f]-thiepin is reduced in 98% yield as described in Example I, Step 7.

STEP 8

3-Bromo-8-nitrodibenzo[b,f]-thiepin

3-Bromo-10,11-dihydro-11-hydroxy-8-nitrodibenzo[b,f]thiepin is dehydrated as described in Example I, Step 8, in 81% yield, m.p. 190°–192° C.

STEP 9

3-Cyano-8-nitrodibenzo[b,f]thiepin

3-Bromo-8-nitrodibenzo[b,f]thiepin is reacted with cuprous cyanide as described in Example I, Step 9, in 69.5% yield, m.p. 234°–236° C.

STEP 10

8-Nitrodibenzo[b,f]thiepin-3-carboxylic Acid

3-Cyano-8-nitrodibenzo[b,f]thiepin is hydrolyzed as described in Example I, Step 10, m.p. 304°–306° C.
Calculated: C: 60.19; H: 3.03; N: 4.68; S: 10.71.
Found: C: 59.68; H: 3.08; N: 4.57; S: 10.75.

EXAMPLE 16

8-Nitrodibenzo[b,f]thiepin-3-carboxylic Acid 5-oxide
400 Mg. 8-nitrodibenzo[b,f]thiepin-3-carboxylic acid is stirred for 24 hours in 200 cc. acetic acid and 1.5 cc. 30% hydrogen peroxide. The product is filtered, washed with water and dried to yield 315 mg. (74%) of pure product, m.p. 278°–281° C.

EXAMPLE 17

STEP 1

3-Cyano-8-nitrodibenzo[b,f]thiepin-5,5-dioxide
2 G. 3-cyano-8-nitrodibenzo[b,f]thiepin is dissolved in 600 cc. chloroform and 12 g. m-chloroperbenzoic acid added. The solution is stirred for 24 hours. Excess powdered calcium hydroxide is added, the mixture filtered through celite, the filtrate evaporated to dryness and the residue chromatographed on silica gel. Elution with 5% ethyl acetate in benzene afforded 1.36 g. (61%) of pure sulfone.

STEP 2

8-Nitrodibenzo[b,f]thiepin-3-carboxylic Acid 5,5-dioxide
400 Mg. 3-cyano-8-nitrodibenzo[b,f]thiepin-5,5-dioxide is refluxed in 5 cc. acetic acid and 5 cc. 50% aqueous sulfuric acid for 24 hours. The mixture is cooled down, the crystallized material is filtered, washed with water, dried at 135° C. in vacuum to yield 345 mg. (81.2%) acid, m.p. 310°–312° C.
Calculated: C: 54.38; H: 2.72; N: 4.22; S: 9.68.

Found: C: 54.31; H: 2.97; N: 4.24; S: 9.69.

EXAMPLE 18

STEP 1

8-Amino-3-cyanodibenzo[b,f]thiepin
5.6 G. 3-cyano-8-nitrodibenzo[b,f]thiepin is dissolved in 600 cc. tetrahydrofuran and 27 g. stannous chloride dihydrate in 40 cc. water is added, followed by 100 cc. concentrated hydrochloric acid. The mixture is stirred for 24 hours, poured onto ice, and shaken with 300 cc. 20% sodium hydroxide. The organic layer is separated and the aqueous basic layer shaken once more with tetrahydrofuran. The combined organic extracts are dried and the solvent evaporated to dryness and the residue chromatographed on silica gel and eluted with 20% ethyl acetate in benzene to yield 2.45 g. of the pure amine, m.p. 188°–190° C.

STEP 2

8-Aminodibenzo[b,f]thiepin-3-carboxylic Acid Hydrochloride Salt

850 Mg. 8-amino-3-cyanodibenzo[b,f]-thiepin is refluxed in a mixture of 20 cc. acetic acid and 20 cc. concentrated hydrochloric acid for 48 hours. The suspended solid is filtered, washed with some acetic acid, dried overnight under vacuum at 70° C. to yield 600 mg. pure compound, m.p. 308°–311° C.
Calculated: C: 58.92; H: 3.95; N: 4.58; Cl: 11.59; S: 10.48.
Found: C: 58.65; H: 4.17; N: 4.49; Cl: 11.66; S: 10.35.

EXAMPLE 19

STEP 1

8-Amino-3-cyanobibenzo[b,fthiepin-5,5-dioxide
875 Mg. 3-cyano-8-nitrodibenzo[b,f]thiepin-5,5-dioxide are dissolved in 105 cc. tetrahydrofuran. 15 CC. concentrated hydrochloric acid is added, followed by 3.8 g. stannous chloride dihydrate and the mixture is stirred for 24 hours. A solution of 20% sodium hydroxide is added, the mixture is shaken and the organic layer separated; the aqueous phase extracted once with ethyl acetate. The combined organic extracts are dried over sodium sulfate and evaporated to dryness. The residue is chromatographed on silica gel to yield 464 mg. (58%) pure amino compound, m.p. 321°–324° C.

STEP 2

8-Aminodibenzo[b,f]thiepin-3-carboxylic Acid 5,5-dioxide Hydrochloride

415 Mg. 8-amino-3-cyanodibenzo[b,f]thiepin-5,5-dioxide is suspended in a mixture of 15 cc. concentrated hydrochloric acid and 15 cc. acetic acid and refluxed for 24 hours. The reaction mixture is evaporated to dryness and the residue collected and dried at 100° C. at 0.5 mm./Hg. to yield 454 mg. pure product, m.p. 280° C.
Calculated: C: 53.33; H: 3.58; N: 4.14; Cl: 10.49; S: 9.49.
Found: C: 53.30; H: 3.32; N: 4.28; Cl: 10.47; S: 9.65.

EXAMPLE 20

STEP 1

8-Chloro-3-cyanodibenzo[b,f]thiepin
1 G. 8-amino-3-cyanodibenzothiepin is suspended in 16 cc. concentrated hydrochloric acid and 5 cc. of water. The suspension is maintained at a temperature between 0° and 5° C. and 300 mg. sodium nitrite in 2 cc. of cold water is added slowly. The reaction mixture is stirred for ½ hour. A mixture of 400 mg. cuprous chloride and 700 mg. cupric chloride dihydrate is then added slowly. After the evolution of nitrogen has subsided, the reaction mixture is stirred at room temperature for 20 minutes, water added and the reaction mixture extracted with chloroform, dried over sodium sulfate and evaporated to dryness to yield 995 mg. (92%) of the pure chloro derivative, m.p. 207°-210° C.

STEP 2

8-Chlorodibenzo[b,f]thiepin-3-carboxylic Acid

550 Mg. 8-chloro-3-cyanodibenzo[b,f]thiepin is refluxed for 16 hours in a mixture of 15 cc. acetic acid and 15 cc. 50% aqueous sulfuric acid. The reaction mixture is cooled down and the product filtered, washed with water, and dried to yield 485 mg. (82% of the pure acid, m.p. 302°-304° C.

Calculated: C: 62.39; H: 3.14; Cl: 12.27; S: 11.10.
Found: C: 62.48; H: 3.06; Cl: 12.01; S: 10.89.

EXAMPLE 21

STEP 1

8-Chloro-3-cyanodibenzo[b,f]thiepin-5,5-dioxide

400 Mg. 8-chloro-3-cyanodibenzo[b,f]thiepin is dissolved in 30 cc. chloroform and 2 g. m-chloroperbenzoic acid added, and the solution stirred for 24 hours. 5 G. calcium hydroxide is added, the mixture stirred for five minutes and filtered through celite. The organic filtrate is evaporated to dryness and the residue chromatographed on silica gel and eluted with 5% ethyl acetate/benzene mixture to yield 339 mg. (76%) pure sulfone, m.p. 228°-230° C.

STEP 2

8-Chlorodibenzo[b,f]thiepin-3-carboxylic Acid 5,5-dioxide

320 Mg. 8-chloro-3-cyanodibenzo[b,f]thiepin-5,5-dioxide is refluxed for 24 hours in a mixture of 10 cc. acetic acid and 10 cc. 50% aqueous sulfuric acid. The mixture is cooled down and the crystalline product filtered, washed with water and dried at 70° C., 0.5 mm./Hg., to yield 289 mg. (82%) of pure acid, m.p. 276°-278° C.

Calculated: C: 56.17%; H: 2.82; Cl: 11.05; S: 9.99.
Found: C: 56.19; H: 3.09; Cl: 10.82; S: 9.82.

EXAMPLE 22

8-Hydroxydibenzo[b,f]thiepin-3-carboxylic Acid

The diazonium chloride, prepared from 1 g. 8-amino-3-cyanodibenzo[b,f]thiepin, is heated at 90° C. for three to four hours in 50 cc. 50% aqueous sulfuric acid. The reaction mixture is cooled down, extracted with ethyl acetate, dried, evaporated and the residue chromatographed on silica gel and eluted with a mixture of ammonium hydroxide, chloroform, methanol, in the ratio of 1:8:4 to yield 250 mg. of the pure phenol.

EXAMPLE 23

8-Hydroxydibenzo[b,f]thiepin-3-carboxylic Acid 5,5-dioxide

The diazonium chloride, prepared from 1 g. 8-amino-3-cyanodibenzo[b,f]thiepin-5,5-dioxide, is treated as per Example 22 to yield 300 mg. of the desired compound.

EXAMPLE 24

8-Mercaptodibenzo[b,f]thiepin-3-carboxylic Acid

A cold solution of the diazonium chloride (see Example 22) is added at a fair rate to a solution of 1 g. potassium thioxanthate in 15 cc. water, maintained at 45°-65° C. At the end of the addition, 10 cc. 40% potassium hydroxide and 10 cc. ethanol are added and the reaction mixture is refluxed for three hours, cooled down, acidified with hydrochloric acid and extracted with ethyl acetate. The organic extract is dried, evaporated to dryness and the residue chromatographed on silica gel and eluted with a mixture of ammonium hydroxide, chloroform, methanol, in the ratio of 1:8:4, to yield 500 mg. of the mercapto acid.

EXAMPLE 25

8-Mercaptodibenzo[b,f]thiepin-3-carboxylic Acid 5,5-dioxide

A cold solution of the diazonium chloride of Example 22 is treated in an identical fashion to Example 24 to yield 450 mg. of the desired compound.

EXAMPLE 26

8-Methoxydibenzo[b,f]thiepin-3-carboxylic Acid

1 G. 8-hydroxydibenzo[b,f]thiepin-3-carboxylic acid is stirred in 50 cc. dimethylformamide with 1.5 g. potassium carbonate and 3 cc. methyl iodide. 100 cc. water is added to the reaction mixture, heated for three hours and then extracted with ethyl acetate, and the aqueous layer acidified. The precipitated solid is filtered, washed with water and a small volume of cold methanol, and dried. Yield of the desired material 700 mg.

EXAMPLE 27

8-Thiomethoxydibenzo[b,f]thiepin-3-carboxylic Acid

1 G. 8-mercaptodibenzo[b,f]thiepin-3-carboxylic acid was treated as per Example 26 to yield 650 mg. of the desired compound.

EXAMPLE 28

8-Methoxydibenzo[b,f]thiepin-3-carboxylic Acid 5,5-dioxide

1 G. 8-hydroxydibenzo[b,f]thiepin-3-carboxylic 5,5-dioxide acid is treated as per Example 26 to yield 830 mg. product.

EXAMPLE 29

8-Thiomethoxydibenzo[b,f]thiepin-3-carboxylic Acid 5,5-dioxide

1 G. 8-mercaptodibenzo[b,f]thiepin-3-carboxylic acid 5,5-dioxide is treated as per Example 26 to yield 650 mg. of the desired compound.

EXAMPLE 30

8-Methylsulfinyldibenzo[b,f]thiepin-3-carboxylic Acid 5,5dioxide

500 Mg. 8-thiomethoxydibenzo[b,f]thiepin-3-carboxylic acid in 15 cc. acetic acid and 3 cc. 30% hydrogen peroxide is stirred at room temperature for 8 hours. 15 CC. water is added to the reaction mixture and the suspended solid filtered and dried to afford 450 mg. of the desired compound.

EXAMPLE 31

8-Methsulfinyldibenzo[b,f]thiepin-3-carboxylic Acid 5,5-dioxide

450 Mg. 8-thiomethoxydibenzo[b,f]thiepin-3-carboxylic acid 5,5-dioxide is stirred at room temperature in 15 cc. acetic acid and 1.5 cc. 30% hydrogen peroxide for an 8 hour period. Water is added and the white solid filtered, washed with water and dried to afford 400 mg. of the desired compound.

EXAMPLE 32

8-Methylsulfonyldibenzo[b,f]thiepin-3-carboxylic Acid 5,5-dioxide

1 G. 8-thiomethoxydibenzo[b,f]thiepin-3-carboxylic acid 5,5-dioxide is heated at 80°-100° C. in 15 cc. acetic acid and 3 cc. 30% hydrogen peroxide. The reaction mixture is cooled down, water added, and the solid filtered and dried to yield 800 mg. of product.

EXAMPLE 33

8-Acetyl-3-cyano-10,11-dihydrodibenzo[b,f]thiepin

Add 125.5 g. (0.94 mole) of aluminum chloride and 47.9 g. (0.47 mole) of acetic anhydride to 1.01 of dichloroethane. Stir at room temperature for 10 minutes. Add 14 g. (0.058 mole) of 3-cyano-10,11-dihydrodibenzo[b,f]thiepin in portions. Stir at room temperature for 4 hours. Pour the reaction mixture over ice and extract into ethyl acetate. Wash with water, dry over sodium sulfate, filter and evaporate to dryness to obtain the title product. (m.p. 138°-141° C.)

EXAMPLE 34

8-Acetyl-10,11-dihydrodibenzo[b,f]thiepin-3-carboxylic Acid

Add 8.5 g. of the nitrile of Example 33 to a mixture of 220 ml. of acetic acid (glacial) and 220 ml. of 50% sulfuric acid. Heat the mixture at reflux under a nitrogen atmosphere overnight. Cool to room temperature and separate the solids by filtration. Recrystallize from acetic acid to obtain the title product. (m.p. 230°-232° C.)

EXAMPLE 35

8-Acetyl-3-cyano-10,11-dihydrodibenzo[b,f]thiepin-5,5-dioxide

Dissolve 2.5 g. of 8-acetyl-3-cyano-10,11-dihydrodibenzo[b,f]thiepin in 200 cc. of methylene chloride and add 6.0 g. of m-chloroperbenzoic acid. Stir at room temperature overnight. Add 12.0 g. of calcium hydroxide and filter through celite. Evaporate to dryness to obtain the title product. (Yield 2.58 g.-92.5%).

EXAMPLE 36

8-Acetyl-10,11-dihydrodibenzo[b,f]thiepin-3-carboxylic Acid 5,5-Dioxide

Suspend 2.2 g. of 8-acetyl-3-cyano-10,11-dihydrodibenzo[b,f]thiepin-5,5-dioxide in 60 ml. of acetic acid and 60 ml. of 50% sulfuric acid. Reflux under a nitrogen atmosphere for 6 hours. Cool to room temperature. Evaporate the acetic acid, dilute with water and separate the solids by filtration. Wash with water and air dry. Suspend the solid in ether (200 ml.), stir at room temperature and filter to obtain the title product. (m.p. 219°-221° C.)

EXAMPLE 37

8-Acetamido-10,11-dihydrodibenzo[b,f]thiepin-3-carboxylic Acid

STEP 1

Oxime of 8-Acetyl-10,11-dihydrodibenzo[b,f]thiepin-3-carboxylic Acid

Reflux for 24 hours a mixture of 130 mg. of 8-acetyl-10,11-dihydrobenzo[b,f]thiepin-3-carboxylic acid, 180 mg. of hydroxylamine hydrochloride and 426 mg. of sodium acetate in 10 cc. of ethanol. Dilute with water and separate the solids by filtration. Wash with water and dry in order to obtain the title product.

STEP 2

8-Acetamido-10,11-dihydrodibenzo[b,f]thiepin-3-carboxylic Acid

Reflux 100 mg. of the oxime from Step 1 in 2 cc. of trifluoroacetic acid for 2 hours. Evaporate to dryness. Add water and extract into ether. Dry and evaporate to dryness to obtain the title product.

EXAMPLE 38

8-Amino-10,11-dihydrodibenzo[b,f]thiepin-3-carboxylic Acid

Reflux 200 mg. of 8-acetamido-10,11-dihydrodibenzo[b,f]thiepin-3-carboxylic acid for 16 hours in a mixture of 5 cc. of acetic acid and 5 cc. of 50% aqueous sulfuric acid. Dilute with water and separate the solids by filtration. Wash with water and dry to obtain the title product.

EXAMPLE 39

10,11-Dihydrodibenzo[b,f]thiepin-3,8-dicarboxylic Acid 5,5-Dioxide

Add 1.85 g. of 8-acetyl-10,11-dihydrobenzo[b,f]thiepin-3-carboxylic acid to a stirred mixture of 370 ml. of 50% aqueous sodium hypochlorite and 13 ml. of 20% aqueous sodium hydroxide at 60° C. Raise the temperature to 85° C. and stire for 30 minutes. Pour the mixture over ice and add sodium metabisulfite Acidify with 6N hydrochloric acid. Separate the solids by filtration wash with water and dry to obtain the title product. (m.p. 350°-352° C.)

EXAMPLE 40

Dibenzo[b,f]thiepin-3,8-dicarboxylic Acid 5,5-Dioxide

Add 2 g. of 8-acetyl-10,11-dihydrodibenzo[b,f]thiepin-3-carboxylic acid to a stirred solution of 50% sodium hypochlorite (400 ml.) and 15 ml. of 20% aqueous sodium hydroxide at 60° C. Heat for 48 hours at 75° C. Cool to room temperature and add sodium metabisulfite. Acidify and separate the solids by filtration. Purify by chromotography over silica gel eluting with a mixture of 80 parts toluene, 20 parts dioxane and 4 parts acetic acid. (m.p. ~375° C.)

EXAMPLE 41

Methyl 10,11-Dihydro-11-oxodibenzo[b,f]thiepin-3-carboxylate

STEP 1

3-Chlorocarbonyl-10,11-dihydro-11-oxodibenzo[b,f]thiepin

Dissolve 5.16 gm. of 10,11-dihydro-11-oxodibenzo[b,f]thiepin-3-carboxylic acid in 100 cc. of chloroform and 50 cc. of thionyl chloride and add to the mixture 1.0 cc. of dimethylformamide. Allow the mixture to stand at room temperature for 72 hours. Evaporate the mixture to dryness to obtain the desired acid chloride.

STEP 2

Methyl 10,11-dihydro-11-oxodibenzo[b,f]thiepin-3-carboxylate

Dissolve 2.0 of the acid chloride of Step 1 in 20 cc. of tetrahydrofuran containing 1.0 cc. of methanol and 4 cc. of pyridine. Allow the mixture to stand at room temperature for 24 hours then evaporate to dryness. Dissolve the residue in 1:4 ether/hexane and filter through silica gel. Evaporate the filtrate to dryness to obtain the title product.

Employing the process of Example 41, but substituting another lower alkanol such as, for example, ethanol, 2-propanol butanol and 2-butanol, for the methanol of Step 2, the corresponding loweralkyl esters of 10,11-dihydro-11-oxodibenzo[b,f]thiepin-3-carboxylic acid are obtained.

Loweralky esters of 10,11-dihydrobenzo[b,f]thiepin-3-carboxylic acid and dibenzo[b,f]thiepin-3-carboxylic acid are prepared by following the process of Example 41 by substituting the desired 3-carboxylic acid for the starting material of Step 1.

EXAMPLE 42

10,11-Dihydro-11-oxodibenzo[b,f]thiepin-3-carboxamide

STEP 1

3-Chlorocarbonyl-10,11-dihydro-11-oxodibenzo[b,f]thiepin

Heat a solution of 5 g. of 10,11-dihydro-11-oxodibenzo[b,f]thiepin-3-carboxylic acid and 40 ml. of thionyl chloride under reflux for 20 minutes. Evaporate the reaction mixture under vacuum to dryness. Repeat the evaporation with two 30 ml. portions of carbon tetrachloride. Crystallize the residue from diisopropyl ether to obtain the title product.

STEP 2

10,11-Dihydro-11-oxodibenzo[b,f]thiepin-3-carboxamide

Dissolve the acid chloride from Step 1 in 20 ml. of dry tetrahydrofuran and add this solution dropwise with stirring to a cooled (ice-bath) saturated solution of ammonia in 60 ml. of tetrahydrofuran. Pass ammonia through the reaction for 15 minutes. Stir at room temperature for an additional 15 minutes and evaporate the reaction mixture to dryness. Add a mixture of 12 ml. of ethanol and 60 ml. of water to the residue and stir at room temperature for an additional 30 minutes. Separate the solid by filtration and wash with water, then with ethanol and then with ether. Dry in vacuo to obtain the title product.

Carboxamides of 10,11-dihydrodibenzo[b,f]thiepin-3-carboxylic acid or dibenzo[b,f]thiepin-3-carboxylic acid are prepared by the process of Example 42, by substituting the desired 3-carboxylic acid for the starting material of Step 1.

EXAMPLE 43

10,11-Dihydro-11-oxodibenzo[b,f]thiepin-3N-methyl-carboxamide

Add 6.0 gm. of 3-chlorocarbonyl-10,11-dihydro-11-oxodibenzo[b,f]thiepin to 4 gm. of methylamine in 100 ml. of methylene chloride at 0°-5° C. Add 13 ml. of triethylamine dropwise over 10 minutes then stir the reaction mixture at room temperature overnight. Extract the reaction mixture with water, dry the organic layer and evaporate to dryness. Chromatograph over silica gel eluting with 200:20 toluene/dioxane. Evaporate eluate to dryness and recrystallize residue from methanol to obtain the title compound.

In a similar manner, substituting another N-loweralkylamine such as, for example, ethylamine, propylamine, isopropylamine, butylamine and the like, or a N,N-diloweralkylamine such as, for example, dimethylamine, diethylamine, dipropylamine, dibutylamine and the like, for the methylamine employed above, there is obtained the corresponding 10,11-dihydro-11-oxodibenzo[b,f]thiepin-3-N-lower alkylcarboxamide or 3-N,N-diloweralkylcarboxamide.

Also in a similar manner, substituting a carboxyloweralkylamine such as, for example, glycine, valine, leucine, isoleucine and the like or the N- derivatives thereof, such as for example, N-methylglycine, N-propylleucine, N-butylisoleucine and the like, there if obtained the corresponding 10,11-dihydro-11-oxodibenzo[b,f]thiepin-3-carboxyloweralky carboxamides or the N-loweralkyl derivatives thereof.

3-N-loweralkylcarboxamides, N,N-diloweralkylcarboxamides and carboxyloweralkylcarboxamides and the N-loweralkyl derivatives thereof corresponding to 10,11-dihydrodibenzo[b,f]thiepin-3-carboxylic acid and dibenzo[b,f]thiepin-3-carboxylic acid are prepared by following the process of Example 43 by substituting the desired 3-chloro-carbonyl compound for the starting material employed in Example 43.

EXAMPLE 44

10,11-Dihydro-11-oxodibenzo[b,f]thiepin-3-N-methanesulfonylcarboxamide

Heat 5.0 gm. of 10,11-dihydro-11-oxodibenzo[b,f]thiepin-3-carboxylic acid in 50 cc. of thionyl chloride for 15 minutes at reflux and then distill off the excess thionyl chloride. Evaporate the residue twice with small volumes of benzene. Add the resulting acid chloride to 4.0 gm. of methane sulphonamide in 100 ml. of methylene chloride at 0°-5° C. Add dropwise over 10 minutes 15 ml. of triethylamine. Stir the mixture at room temperature overnight. Extract the reaction mixture with 100 cc. of 0.5 N sodium hydroxide, wash the alkaline extract with ether and acidify with 6N hydrochloride acid. Separate the solids by filtration and dry in vacuo over potassium hydroxide. Chromatograph over silica gel eluting with 200:20:3 toluene/dioxane/acetic acid. Evaporate the eluate to dryness and recrystallize the residue from methanol to obtain the title product.

In a similar manner, substituting another loweralkylsulfonamide such as, for example, ethanesulphonamide, propane sulphonamide, butane sulphonamide and the like, for the methane sulphonamide employed above, there is obtained the corresponding 10,11-dihydro-11-oxodibenzo[b,f]thiepin-2-N-loweralkysulfonylcarboxamide.

3-N-loweralkylsulfonylcarboxamide derivatives of 10,11-dihydrodibenzo[b,f]thiepin-3-carboxylic acid and dibenzo[b,f]thiepin-3-carboxylic acid are prepared by following the procedure of Example 44 by substituting the desired 3-carboxylic acid for the carboxylic acid starting material in Example 44.

EXAMPLE 45

10,11-Dihydro-11-oxodibenzo[b,f]thiepin-3-(3-methyl-2-thiazolidinylidine)carboxamide Reflux 1.0 gm. of 10,11-dihydro-11-oxodibenzo[b,f]thiepin-3-carboxylic acid in 15 cc. of thionyl chloride for 30 minutes. Strip the reaction mixture to dryness and dissolve the residue in 25 cc. of methylene chloride. Add a solution of 1.0 gm. of 2-imino-3-methylthiazolidine in 10 cc. of methylene chloride. Stir at room temperature for 30 minutes and add water. Continue stirring for 10 minutes. Separate the organic phase and wash with water and dry overnight over sodium sulfate. Strip to dryness. Stir and triturate the residue in ether, then in methanol. Chromatograph the resulting solid over silica gel, eluting with 20% ethylacetate in benzene. Strip to dryness to obtain the title product.

3-(3-Methyl-2-thiazolidinylidine) carboxylates corresponding to 10,11-dihydrodibenzo[b,f]-thiepin-3-carboxylic acid and dibenzo[b,f]thiepin-3-carboxylic acid are prepared by following the procedure of Example 45 by substituting the desired 3-carboxylic acid for the starting material employed in Example 45.

EXAMPLE 46

10,11-Dihydro-11-oxodibenzo[b,f]thiepin-3-(4-hydroxy-$\Delta^3$-pyrroline-3-yl-2,5-dione)

STEP 1

3-Hydroxymethyl-10,11-dihydro-11-oxodibenzo[b,f]thiepin

Dissolve 5.1 gm. of 10,11-dihydro-11-oxodibenzo[b,f]thiepin-3-carboxylic acid in 100 cc. of tetrahydrofuran and add 35 cc. of 1M borane in tetrahydrofuran at room temperature under a nitrogen atmosphere. Stir the mixture at room temperature for 3 hours. Slowly dilute the reaction mixture with water and then with ethyl acetate. Wash with aqueous sodium chloride, dry and evaporate to an oil.

STEP 2

3-Bromomethyl-10,11-dihydro-11-oxodibenzo[b,f]thiepin

Dissolve 4.43 g. of the alcohol of Step 1 in 100 cc. of benzene and add 1 cc. (10.5 mmole) of phosphorous tribromide. Stir at room temperature for 1 hour, add water and then dilute with toluene. Wash three times with water, dry and strip to a solid residue.

STEP 3

3-Cyanomethyl-10,11-dihydro-11-oxodibenzo[b,f]thiepin

Dissolve 6.4 gm. of the bromide of Step 2 in 75 cc. of dimethylformamide and add 2.95 gm. of sodium cyanide. Stir the mixture at room temperature for 1.5 hours. Dilute with 600 cc. of water and extract three times with ether. Wash the combined organics with water, dry and strip to a solid residue. Triturate in hexane and recover the solid by filtration.

STEP 4

10,11-Dihydro-11-oxodibenzo[b,f]thiepin-3-acetic acid

Reflux 2.0 gm. of the nitrile of Step 3 in a mixture of 30 cc. of 20% aqueous sodium hydroxide and 30 cc. of ethanol for four hours. Strip away the alcohol, wash with ethyl acetate and acidify the aqueous phase with hydrochloric acid. Separate the precipitate by filtration. Wash with water and dry.

STEP 5

10,11-Dihydro-11-oxodibenzo[b,f]thiepin-3-acetamide

Reflux for 20 minutes a mixture of 5.0 gm. of the acid of Step 4 and 40 ml. of thionyl chloride. Evaporate to dryness under vacuum. Evaporate twice with 30 ml. portions of carbon tetrachloride. Dissolve the residue in 20 ml. of tetrahydrofuran and add the solution dropwise to a cooled and stirred saturated solution (ice bath) of ammonia in 60 ml. of tetrahydrofuran. Pass ammonia through the solution simultaneously. Continue stirring at room temperature for an additional 15 minutes. Evaporate the mixture to dryness. Add a mixture of 12 ml. of ethanol and 60 ml. of water and stir the suspension for 30 minutes. Separate the solids and wash with water, then with ethanol and finally with ether to obtain the title product.

STEP 6

10,11-Dihydro-11-oxodibenzo[b,f]thiepin-3-(-4-hydroxy-$\Delta^3$-pyrrolin-3-yl-2,5-dione)

Stir at room temperature a mixture of 5.118 gm. of the amide of Step 5, 2.939 gm. of diethyloxalate, 4.723 gm. of potassium t-butoxide and 40 ml. of dimethylformamide for 6 hours. Pour the reaction mixture into 300 ml. of ice-water and extract with 300 ml. of ethyl acetate. Acidify with 6N hydrochloric acid and separate the ethyl acetate layer. Wash with saturated sodium chloride solution and dry. Evaporate to dryness and dissolve the residue in warm dioxane. Treat with a slight excess of ammonia and separate the solid by filtration. Wash with dioxane and dry. Suspend the product in water, acidify with 6N hydrochloric acid and extract with ethyl acetate. Wash the extract with saturated sodium chloride solution, dry over magnesium sulfate and evaporate to obtain the title product.

In a similar manner, substituting 10,11-dihydrodibenzo[b,f]thiepin-3-carboxylic acid or dibenzo[b,f]thiepin-3-carboxylic acid for the carboxylic acid starting material employed in Step 1, there is obtained the corresponding 10,11-dihydrobibenzo[b,f]thiepin-3-(4-hydroxy-$\Delta^3$-pyrrolin-3-yl-2,5-dione) or dibenzo[b,f]thiepin-3-(4-hydroxy-$\Delta^3$-pyrrolin-3-yl-2,5-dione).

EXAMPLE 47

β-Hydroxyethyl 10,11-Dihydro-11-oxodibenzo[b,f]thiepin-3-carboxylate

To a stirred solution of 1.0 gm. of 2-chlorocarbonyl-10,11-dihydro-11-oxodibenzo[b,f]thiepin in 50 cc. of methylene chloride, add 3 gm. of ethylene glycol and stir the mixture for 18 hours at room temperature. Distill off the solvent and excess ethylene glycol under high vacuum (0.1 mm.). Chromatograph the residue on a silica gel column (100 gm.), eluting with 10% ethyl acetate in benzene to obtain the title product.

In a similar manner, substituting another loweralkyldiol such as, for example, trimethylene glycol and 1,4-butanediol and the like for the ethylene glycol, there is obtained the corresponding hydroxyloweralkylester.

Hydroxyloweralkylesters of 10,11-dihydrodibenzo[b,f]thiepin-3-carboxylic acid and dibenzo[b,f]thiepin-3-carboxylic acid are prepared by substituting the desired 3-carboxylic acid for the starting material employed in Example 47.

EXAMPLE 48

β-Dimethylaminoethyl-10,11-Dihydro-11-oxodibenzo[b,f]thiepin-3-carboxylate

Dissolve 1.0 gm. of 3-chlorocarbonyl-10,11- dihydro-11-oxodibenzo[b,f]thiepin as prepared in Example 31, Step 1, in 10 cc. of anhydrous tetrahydrofuran with stirring and add 2 ml. of N,N-dimethylethanolamine. Stir at room temperature for 18 hours and strip the mixture to dryness. Partition the residue between ether and dilute hydrochloric acid and separate the aqueous layer. Basify the aqueous layer with aqueous ammonia and extract with ethyl acetate. Evaporate the organic phase and chromatograph the residue over silica-gel eluting with 90% chloroform in methanol to obtain the title product.

In a similar manner, substituting another N,N-diloweralkylaminoloweralkanol such as, for example, amine, diethylethanolamine, 3-N,N-dimethylaminopropan-1-ol, 4-N,N-diethylaminobutan-1-ol and the like, for the N,N-dimethylethanolamine, there is obtained the corresponding N,N-diloweralkylaminoloweralkyl ester.

N,N-diloweralkylaminoloweralkyl esters of 10,11-dihydrodibenzo[b,f]thiepin-3-carboxylic acid and dibenzo[b,f]thiepin-3-carboxylic acid are prepared by following the procedure of Example 48 and substituting the desired 3-chlorocarbonyl compound for the chlorocarbonyl starting material employed in Example 48.

EXAMPLE 49

10,11-Dihydro-11-oxodibenzo[b,f]thiepin-3-N-carboxymethylcarboxamide

Reflux 1.0 gm. of 3-chlorocarbonyl-10,11-dihydro-11-oxodibenzo[b,f]thiepin in 20 cc. of ethyl acetate containing 2.0 gm. of glycine for 5 hours. Evaporate the mixture to dryness. Add 30 cc. of water to the solid residue and stir at room temperature for one hour. Separate the solid by filtration and recrystallize from ethanol to obtain the title product.

In a similar manner, substituting another amino acid such as, for example, alanine or valine and the like for the glycine, there is obtained the corresponding 3-carboxyloweralkylcarboxamide, Carboxyloweralkylcarboxamides of 10,11-dihydrodibenzo[b,f]thiepin-3-carboxylic acid and dibenzo[b,f]thiepin-3-carboxylic acid are prepared by substituting the desired 3-chlorocarbonyl compound for the starting material employed in Example 49.

EXAMPLE 50

β-Carboxyethyl 10,11-Dihydro-11-oxodibenzo[b,f]thiepin-3-carboxylate

Dissolve 1.0 gm. of 3-chlorocarbonyl-10,11-dihydro-11-oxodibenzo[b,f]thiepin in 20 cc. of tetrahydrofuran and add 1.0 gm. of the sodium salt of β-hydroxypropionic acid. Stir the mixture at room temperature for 18 hours. Filter and evaporate the filtrate to dryness. Recrystallize the solid residue from ethanol to obtain the title product.

In a similar manner, substituting another hydroxyloweralkanoic acid salt such as, for example, an alkali metal salt of hydroxyacetic acid, 3-hydroxypropionic acid sodium salt, there is obtained the corresponding carboxyloweralkyl-3-carboxylate ester.

Carboxyloweralkyl-3-carboxylate esters of 10,11-dihydrodibenzo[b,f]thiepin-3-carboxylic acid and dibenzo [b,f]thiepen-3-carboxylic acid are prepared by substituting the desired 3-chlorocarbonyl compound for the starting material employed in Example 50.

EXAMPLE 51

3-(3-Hydroxy-1,2,5-thiadiazol-4-yl)-10,11-dihydro-11-oxo-dibenzo[b,f]thiepin

STEP 1

3-Cyano-10,11-dihydro-11-oxodibenzo[b,f]thiepin

Stir 5 gm. of methyl 10,11-dihydro-11-oxodibenzo[b,f]thiepin-3-carboxylate in 500 ml. of methanol saturated with ammonia gas for 24 hours at room temperature. Evaporate the reaction mixture to dryness. Reflux the residue in 200 ml. of methylene chloride containing 10 gm. of phosphorous oxychloride for eight hours. Cool the reaction mixture to room temperature and shake several times with water. Separate the organic layer, dry over magnesium sulfate and evaporate to dryness to obtain the title product.

STEP 2

10,11-Dihydro-11-oxodibenzo[b,f]thiepin-3-carboxyaldehyde

Heat a mixture of 5.0 gm. of 3-cyano-10,11-dihydro-11-oxodibenzo[b,f]thiepin and 4.0 gm. of Raney nickel alloy in 60 ml. of 75% (v/v) aqueous formic acid at reflux for 1.5 hours. Cool to room temperature and filter. Concentrate to small volume and extract with methylene chloride. Wash the extract with water and with 1N sodium bicarbonate until neutral. Dry the neutral extract over sodium sulfate and concentrate to dryness to obtain the title product.

STEP 3

10,11-Dihydro-11-oxodibenzo[b,f]thiepin-3-(2-aminoacetonitrile)

Stir at room temperature for 12 hours a mixture of 5.85 gm. of ammonium chloride, 5.3 gm. of sodium cyanide, 75 ml. of ammonium hydroxide, 100 ml. of ethanol saturated with ammonia and 12 gm. of carboxaldehyde of Step 1. Pour the reaction mixture into 300 ml of water and extract with ether. Dry the extract over sodium sulfate and concentrate to dryness to obtain the title product.

STEP 4

10,11-Dihydro-11-oxodibenzo[b,f]thiepin-3-(2-aminoacetamide)

Stir at room temperature 5.0 gm. of the aminoacetonitrile of Step 2 in 30 ml. of concentrated hydrochloric acid for 30 minutes. Slowly pour the reaction mixture into cold ammonium hydroxide. Extract the mixture with ether and dry over sodium sulfate. Evaporate the extract to dryness to obtain the title product.

STEP 5

3-(3-Hydroxy-1,2,5-thiadiazol-4-yl)-10,11-dihydro-11-oxodibenzo[b,f]thiepin

Stir overnight at room temperature a mixture of 1.365 gm. of the aminoacetamide of Step 4, 1,989 gm. of sulfur monochloride and 5 ml. of dimethylformamide. Filter the reaction mixture and then partition between ice-water (75 ml.) and ethyl acetate (75 ml.). Filter, separate the organic layer, wash with saturated aqueous sodium chloride solution and dry over magnesium sulfate. Evaporate to dryness and dissolve the residue in 200 ml. of boiling ethanol, treat with charcoal and filter. Concentrate to 25 ml. and separate the solids by filtration to obtain the title product.

Similarly by substituting 3-cyano-10,11-dihydrodibenzo[b,f]thiepin or 3-cyanodibenzo[b,f]thiepin for the 3-cyano-10,11-dihydro-11-oxo-dibenzo[b,f]thiepin employed in Step 2, there is obtained the corresponding 3-(3-hydroxy-1,2,5-thiadiazol-4-yl)-10,11- dihydrodibenzo[b,f]thiepin or 3-(3-hydroxy-1,2,5-thiadiazol-4-yl)-dibenzo[b,f]thiepin. The required cyano intermediates are prepared by substituting the appropriate 3-carboxylic acid methyl ester for the methyl 10,11-dihydro-11-oxodibenzo[b,f]thiepin-3-carboxylate employed in Step 1 above.

EXAMPLE 52

3-(1H-Tetrazol-5-ylmethyl)-10,11-dihydro-11-oxodibenzo[b,f]thiepin

Add to 25 cc. of tetrahydrofuran cooled in an ice bath 1.59 gm. (11.9 mmole) of aluminum chloride, 1.33 gm. (5.25 mmole) of 3-cyanomethyl-10,11-dihydro-11-oxodibenzo[b,f]thiepin and 1.55 gm. (23.8 mmole) of sodium azide. Reflux the mixture for 19 hours, cool, dilute with water and acidify. Extract the mixture into ethyl acetate and evaporate. Triturate the residue in ether and separate the title product by filtration.

EXAMPLE 53

10,11-Dihydro-11-oxodibenzo[b,f]thiepin-3-acetic Acid-11,11-dioxide

Heat 600 mg. of 10,11-dihydro-11-oxodibenzo[b,f]thiepin-3-acetic acid to 80°–85° C. in a mixture of 30 cc. of glacial acetic acid and 5 cc. of 30% hydrogen peroxide for 3 hours. Dilute with water to a final volume of about 250 cc. Separate the title product by filtration.

The compounds of formula I are useful in the treatment or prophylaxis of mammalian disease conditions where excessive undesirable contractile activity of prostaglandins, such as $PGF_{2\alpha}$, or prostaglandin biosynthetic intermediates contribute. These conditions include asthma, inflammatory states such as arthritis, allergy, diarrhea, hypertension, angina, platelet aggregation, cerebral spasm, premature, abortion and dismenorrhea. In particular, they are of value in reaginic mediated asthma (extrinsic asthma).

The magnitude of a prophylactic or therapeutic dose of compound of formula I will, of course, vary with the nature and the severity of the condition to be treated and with the particular compound of formula I and its route of administration. In general, the dose range lies within the range of 0.2 mg. to 100 mg. per kg. body weight of a mammal.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg. (preferably 1 to 5 mg.) of a compound of formula I per kg. of body weight per day and in the case where an oral composition is employed a suitable dosage range is about, e.g., 1 to 50 mg. of a compound of formula I per kg. of body weight per day, preferably from 10 to 40 mg./kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets, may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 50 mg. to 500 mg. of the active ingredient and each cachet or capsule contains from 50 mg. to 500 mg. of the active ingredient.

Although the instant invention has been described in the foregoing specification in terms of the use of the novel thiepin disclosed herein in the treatment and control of human and warmblooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chronic obstructive lung disease (e.g., asthma), prostaglandins play a role in other allergic conditions as well as in inflammation, diarrhea, hypertension, angina, cerebral spasm, premature abortion and dismenorrhea. Also, the thiepins of this invention are potent $TXA_2$ biosynthesis inhibitors, inhibiting platelate aggregation, and can be useful in diseases such as atherosclerosis, variant anginal and myocardial infarction. Applicants consider application of the thiepins disclosed and claimed herein to the treatment and control of such disease conditions to be obvious equivalents to the invention as disclosed by applicants and to fall within the scope of the instant invention.

The subject matter which applicants regard as their invention, and which is sought to be patented herein, is particularly pointed out and distinctly claimed as follows:

1. A compound which is 10,11-dihydro-11-oxodibenzo[b,f]thiepin-3-carboxylic acid.
2. A compound which is 10,11-dihydro-11-oxodibenzo[b,f]thiepin-3-carboxylic acid-5-oxide.

* * * * *